US012146174B2

(12) United States Patent
Yamaguchi et al.

(10) Patent No.: US 12,146,174 B2
(45) Date of Patent: Nov. 19, 2024

(54) MUTATED HISTIDINE DECARBOXYLASE AND USE THEREOF

(71) Applicant: AJINOMOTO CO., INC., Tokyo (JP)

(72) Inventors: Hiroki Yamaguchi, Kanagawa (JP); Masayuki Sugiki, Kanagawa (JP); Kunio Nakata, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 18/165,045

(22) Filed: Feb. 6, 2023

(65) Prior Publication Data

US 2023/0295600 A1   Sep. 21, 2023

Related U.S. Application Data

(60) Division of application No. 16/566,236, filed on Sep. 10, 2019, now Pat. No. 11,713,454, which is a continuation of application No. PCT/JP2018/009572, filed on Mar. 12, 2018.

(30) Foreign Application Priority Data

Mar. 13, 2017   (JP) ................................ 2017-047813

(51) Int. Cl.
*C12N 15/70* (2006.01)
*C12N 9/88* (2006.01)
*C12Q 1/527* (2006.01)

(52) U.S. Cl.
CPC .............. *C12N 9/88* (2013.01); *C12N 15/70* (2013.01); *C12Q 1/527* (2013.01); *C12Y 401/01022* (2013.01)

(58) Field of Classification Search
CPC .. C07K 2319/00; C07K 5/1024; C07K 14/24; C12N 9/88; C12N 15/102; C12N 15/62; C12N 15/63; C12N 15/11; C12Y 401/01022; C12Y 203/02
USPC ..................................................... 435/320.1
See application file for complete search history.

(56) References Cited

U.S. PATENT DOCUMENTS

| | | | |
|---|---|---|---|
| 4,425,436 A | 1/1984 | Matsumoto et al. | |
| 2010/0323975 A1 | 12/2010 | Kawano et al. | |
| 2014/0205710 A1 | 7/2014 | Janow | |
| 2016/0370379 A1 | 12/2016 | Endou et al. | |
| 2016/0376580 A1 | 12/2016 | Oonishi et al. | |
| 2017/0206335 A1 | 7/2017 | Nagao et al. | |
| 2020/0002697 A1 | 1/2020 | Yamaguchi et al. | |

FOREIGN PATENT DOCUMENTS

| | | |
|---|---|---|
| CA | 2275886 A1 | 7/1998 |
| JP | 57-141289 A | 9/1982 |
| JP | 2001-242174 A | 9/2001 |
| JP | 2016-512021 A | 4/2016 |
| WO | WO2009/081991 A1 | 7/2009 |
| WO | WO2015/137418 A1 | 9/2015 |
| WO | WO2016/056631 A1 | 4/2016 |
| WO | WO2016/103761 A1 | 6/2016 |

OTHER PUBLICATIONS

Levy, H., "Histidinemia," Orphanet encyclopedia, May 2002, http://www.orpha.net/data/patho/GB/uk-HIS.pdf., pp. 1-5.
Kawai, Y., et al., "Molecular characterization of histidinemia: identification of four missense mutations in the histidase gene," Hum. Genet. 2005;116:340-346.
Sakurabayashi, I., et al., "Laboratory Medicine Encyclopedia & Dictionary," Ishiyaku Publishers, Inc., 2008, pp. 205, with English translation of relevant part.
Hisamatsu, T., et al., "Novel, Objective, Multivariate Biomarkers Composed of Plasma Amino Acid Profiles for the Diagnosis and Assessment of Inflammatory Bowel Disease," PLoS One 2012;7(1):e31131.
Miyagi, Y., et al., "Plasma Free Amino Acid Profiling of Five Types of Cancer Patients and Its Application for Early Detection," PLoS One 2011;6(9):e24143.
Hasebe, Y., et al., "Amperometric flow-type L-histidine sensor using an immobilized galactose oxidase reactor, based on a novel catalytic activity induced by exogenous histidine," Sensors and Actuators B 2000;66:12-15.
Accession No. B7GZJ8 (DCHS_ACIB3), Protein: Histidine decarboxylase, Organism: Acinetobacter baumannii, [online], posting date: Feb. 10, 2009, search date: May 22, 2018, Database UniProt/GeneSeq, <URL: http://www.uniprot.org/uniprot/B7GZJ8>.
Accession No. W9B1E6 (W9B1E6_HLEPN), Protein: Histidine decarboxylase, Organism: Klebsiella pneumoniae, [online], posting date: May 14, 2014, search date: May 22, 2018, Database UniProt, GenSeq, <URL: http://www.uniprot.org/uniprot/W9B1E6>.
Accession No. P05034 (DCHS_MORMO), Protein: Histidine decarboxylase, Organism: *Morganella morganii* (*Proteus morganii*), [online], posting date: Jan. 23, 2007, search date: May 22, 2018, Database UniProt/Gene Seq, <URL: http://www.uniprot.org/uniprot/P05034>.
Accession No. AOAOMOT5M7 (A0A0M0T5M7_9GAMM), Protein: Histidine decarboxylase, Organism: *Xenorhabdus* sp. GDc328, [online], posting date: Nov. 11, 2015, search date: May 22, 2018, Database UniProt/Gene Seq, <URL: http//www.uniprot.org/uniprot/AOAOMOT5M7>.

(Continued)

*Primary Examiner* — Robert B Mondesi
*Assistant Examiner* — Mohammad Y Meah
(74) *Attorney, Agent, or Firm* — Cermak & McGowan LLP; Shelly Guest Cermak

(57) ABSTRACT

The present invention provides a mutated histidine decarboxylase suitable for a practical use. Specifically, the present invention provides a mutated histidine decarboxylase having at least one amino acid residue mutated as compared to a wild-type histidine decarboxylase, and having higher histidine decarboxylase activity and/or stability than the wild-type histidine decarboxylase, and also a use thereof. The mutated histidine decarboxylase has Motifs (1) to (6), and an amino acid residue in at least one motif thereof can be mutated. The mutated histidine decarboxylase can also have a mutation of at least one amino acid residue in an amino acid sequence designated by SEQ ID NO: 3 and in a homologous sequence thereto.

7 Claims, 10 Drawing Sheets

Specification includes a Sequence Listing.

(56) References Cited

OTHER PUBLICATIONS

Accession No. P28577 (DCHS_KLEAE), Protein: Histidine decarboxylase, Organism: *Klebsiella aerogenes*, [online], posting date: Jan. 23, 2007, search date: May 22, 2018, Database UniProt/GeneSeq, <URL: http://www.uniprot.org/uniprot/P28577>.

Accession No. A0A0J6NJE2 (A0A0J6NJE2_9NEIS), Protein: Histidine decarboxylase, Organism: *Chromobacterium* sp. LK11, [online], posting date: Oct. 14, 2015, search date: May 22, 2018, Database UniProt/GeneSeq, <URL: http://www.uniprot.org/uniprot/A0A0J6NJE2>.

Accession No. KC771251, *Morganella morganii* subsp. *morganii* strain DSM 30164 histidine/histamine antiporter (hdcT1), Histidine decarboxylase (hdc), histidine/histamine antiporter (hdcT2), and histidyl-tRNA synthetase (hisRS) genes, complete cds, [online], posting date: Mar. 10, 2014, search date: May 22, 2018, Database UniProt/GeneSeq, <URL: https://www.ncbi.nlm.nih.gov/nuccore/kc771251>.

Accession No. AB259288, Photobacterium phosphoreum hdc gene for histidine decarboxylase, complete cds, strain: YS4-7, [online], posting date: Mar. 3, 2007, search date: May 22, 2018, Database UniProt/GeneSeq, <URL: https://www.ncbi.nlm.nih.gov/nuccore/95113534?sat=3&satkey=6591767>.

Van Poelje, P. D., et al., "Site-Directed Alteration of the Active-Site Residues of Histidine Decarboxylase from Clostridium perfringens," Biochem. 1990;29:10413-10418.

Vaaler, G. L., et al., "Pyridoxal 5'-Phosphate Dependent Histidine Decarboxylase: Overproduction, Purification, Biosynthesis of Soluble Site-Directed Mutant Proteins, and Replacement of Conserved Residues," Biochem. 1989;28:7306-7313.

Ishii, S., et al., "Functionally Important Residues of Aromatic L-Amino Acid Decarboxylase Probed by Sequence Alignment and Site-Directed Mutagenesis," J. Biochem. 1996;120:369-376.

International Search Report and Written Opinion for PCT Patent App. No. PCT/JP2018/009572 (Jun. 5, 2018) with English translation of the ISR.

Extended European Search Report for European Patent App. No. 18767846.1 (Dec. 3, 2020).

Zhou, J., et al., "A portable chemical sensor for histidine based on the strategy of click chemistry," Biosensors and Bioelectronics 2014;51:386-390.

Database Geneseq [Online], Nov. 12, 2009, "Photobacterium phosphoreum protein SEQ ID No. 21244", retrieved from EBI acecssion No. GSP:AXF88876, Database accession No. AXF88876, pp. 1-2.

Database UniProt [Online], Apr. 14, 2009, XP002801123, retrieved from EBI accession No. UNIPROT:B7GZJ8, Database accession No. B7GZJ8, pp. 1-2.

Witkowski, A., et al., "Conversion of a beta-Ketoacyl Synthase to a Malonyl Decarboxylase by Replacement of the Active-Site Cysteine with Glutamine," Biochem. 1999;38:11643-11650.

Whisstock, J. C., et al., "Prediction of protein function from protein sequence and structure," Quarterly Rev. Biophys. 2003;36(3):307-340.

Devos, D., et al., "Practical Limits of Function Prediction," Proteins: Structure, Function, and Genetics 2000;41:98-107.

Hisamatsu, T., et al., "Decreased Plasma Histidine Level Predicts Risk of Relapse in Patients with Ulcerative Colitis in Remission," PLoS ONE 2015;10(10):e0140716, 10 pp.

Decision of Refusal for Japanese Patent App. No. 2019-506026 (Jul. 7, 2022) with English language translation thereof.

Database USPTO Proteins [Online], Dec. 14, 2016 (Dec. 14, 2016), "Sequence 18134 from patent U.S. Pat. No. 9290773," retrieved from EBI accession No. USPOP:APN13725, Database accession No. APN13725, 1 pg.

Communication Pursuant to Article 94(3) EPC from European Patent App. No. 18767846.1 (Feb. 27, 2023).

FIG. 1

|  |  | C G D W A E Y C N Y L L N S F D F E | |
|---|---|---|---|
| 1. | HisDC | | |
| 2. | A0A126VDF4 | C G D W A E Y C N Y L L N S F D F E | (SEQ ID No:8) |
| 3. | A0A0H4U8G4 | C G D W S E Y C N Y L L N S F E F E | (SEQ ID No:14) |
| 4. | A0A0H4U975 | C G D W G E Y C N Y L L N S F D F E | (SEQ ID No:20) |
| 5. | A0A068R0F7 | C G D W S E Y C N Y L L N S F D F E | (SEQ ID No:26) |
| 6. | W9B1E6 | C G D W G A E C N Y L L N S F E F E | (SEQ ID No:32) |
|  |  | C G D W A D Y C N Y R L N T F D F E | (SEQ ID No:38) |
|  |  | | (SEQ ID No:44) |

FIG. 2

| | | | | | | |
|---|---|---|---|---|---|---|
| 1. | HisDC | S W G Y V T N G G T E G N M F G C Y L A R E L F P D | (SEQ ID No:9) |
| 2. | A0A126VDF4 | W G Y V T N G G T E S N M F G C Y L G R E L F P D | (SEQ ID No:15) |
| 3. | A0A0H4U8G4 | W G Y V T N G G T E S N M F G C Y L G R E L F P D | (SEQ ID No:21) |
| 4. | A0A0H4U975 | W G Y V T N G G T E G N M F G C Y L S R E L F P N | (SEQ ID No:27) |
| 5. | A0A068R0F7 | W G Y V T N G G T E G N M F G C Y L A R E L F P D | (SEQ ID No:33) |
| 6. | W9B1E6 | W G Y V T N G G T E G N M F G C Y L G R E L F P D | (SEQ ID No:39) |
| 7. | A0A0F7XYJ8 | W G Y V T N G G T E G N M F G C Y L A R E L F P D | (SEQ ID No:45) |
| 8. | A0A0J6NJE2 | W G Y V T N G G T E G N M F G C Y L A R E L F P D | (SEQ ID No:50) |
| 9. | A0A0W0AK78 | W G Y V T N G G T E G N M Y S C Y L A R E L F P E | (SEQ ID No:55) |
| 10. | U4DVA0 | W G Y V T N G G T E G N M F G C Y L A R E L F P N | (SEQ ID No:58) |
| 11. | A0A0F4P2Z8 | W G Y V T N G G T E G N M Y G C Y L A R E R F P D | (SEQ ID No:61) |
| 12. | A0A1B1VGV7 | W G Y V T N G G T E G N M Y G C Y L A R E R F P D | (SEQ ID No:64) |
| 13. | A0A096BDC0 | W G Y F T S G S T E S N L F G C Y L A R E R F K N | (SEQ ID No:65) |
| | | | (SEQ ID No:66) |

FIG. 3

| | | | | | | | | | | | | | | | | | | | | |
|---|---|---|---|---|---|---|---|---|---|---|---|---|---|---|---|---|---|---|---|---|
| 1. | HisDC | I | | G | S | R | N | G | H | T | P | L | M | M | W | E | A | I | K | S |
| 2. | A0A126VDF4 | | T | G | S | R | N | G | H | T | P | L | M | M | W | C | A | V | K | S |
| 3. | A0A0H4U8G4 | | T | G | S | R | N | G | H | T | P | L | M | M | W | E | A | I | K | S |
| 4. | A0A0H4U975 | | S | G | S | R | N | G | H | T | P | L | M | M | W | E | A | V | K | S |
| 5. | A0A068R0F7 | | T | G | S | R | N | G | Q | T | P | L | M | M | W | E | A | I | R | S |
| 6. | W9B1E6 | | T | G | S | R | N | G | H | T | P | L | M | M | W | A | A | I | R | S |
| 7. | A0A0F7XYJ8 | | S | G | S | R | N | G | H | T | P | L | M | M | W | E | A | L | R | S |

(SEQ ID No:10)
(SEQ ID No:16)
(SEQ ID No:22)
(SEQ ID No:28)
(SEQ ID No:34)
(SEQ ID No:40)
(SEQ ID No:46)
(SEQ ID No:51)

FIG. 4

| | | R F Q A A G I N A W R N K N S I T V V F | |
|---|---|---|---|
| 1. | HisDC | R F Q A A G I N A W R N K N S I T V V F | |
| 2. | A0A126VDF4 | L Q T A G I N A W C N K N S I T V V F | (SEQ ID No:11) |
| 3. | A0A0H4U8G4 | L Q S A G V N A W R N K N S I T V V F | (SEQ ID No:17) |
| 4. | A0A0H4U975 | F Q S A G I D A W R N K N S I T V V F | (SEQ ID No:23) |
| 5. | A0A068R0F7 | F Q K A G I D A W R N K N S I T V V F | (SEQ ID No:29) |
| 6. | W9B1E6 | F R A A G I N A W R H D N S I T V J F | (SEQ ID No:35) |
| 7. | A0A0F7XYJ8 | F Q K A G I N A W R N K N S I T V V F | (SEQ ID No:41) |
| 8. | A0A0J6NJE2 | L R A A G I D A W R N P N S I T V V F | (SEQ ID No:47) |
| 9. | A0A0W0AK78 | F Q A A G I Q A W R C K N S I T V V F | (SEQ ID No:52) |
| 10. | U4DVA0 | F H A K G I H A W R N P N S I T V V F | (SEQ ID No:56) |
| | | L K S K G V P A W L N P N S V J V V F | (SEQ ID No:59) |
| | | | (SEQ ID No:62) |

FIG. 5

| | | N K N S I T V V F P C P S E A | |
|---|---|---|---|
| 1. | HisDC | | |
| 2. | A0A126VDF4 | K N S I T V V F P C P S E A | (SEQ ID No:12) |
| 3. | A0A0H4U8G4 | K N S I T V V F P C P S E A | (SEQ ID No:18) |
| 4. | A0A0H4U975 | K N S I T V V F P C P S E A | (SEQ ID No:24) |
| 5. | A0A068R0F7 | K N S I T V V F P C P S E D | (SEQ ID No:30) |
| 6. | W9B1E6 | D N S I T V V F P C P S V A | (SEQ ID No:36) |
| 7. | A0A0F7XYJ8 | K N S I T V J F P C P S E S | (SEQ ID No:42) |
| 8. | A0A0J6NJE2 | P N S I T V V F P C P S A N | (SEQ ID No:48) |
| 9. | A0A0W0AK78 | K N S I T V V F P S P S E P | (SEQ ID No:53) |
| 10. | U4DVA0 | P N S I T V V F P K P A D H | (SEQ ID No:57) |
| | | P N S V I V V F P T P T E A | (SEQ ID No:60) |
| | | | (SEQ ID No:63) |

FIG. 6

| | | E A V W K K H C L A T S G . I | |
|---|---|---|---|
| 1. | HisDC | E A V W K K H C L A T S G . I | |
| 2. | A0A126VDF4 | E A V W K K H C L A T S G G Q | (SEQ ID No:13) |
| 3. | A0A0H4U8G4 | E A V W K K H C L A T S G E V | (SEQ ID No:19) |
| 4. | A0A0H4U975 | E A V W K K H C L A T S G D I | (SEQ ID No:25) |
| 5. | A0A068R0F7 | E D V W K K H C L A T S N G L | (SEQ ID No:31) |
| 6. | W9B1E6 | V A V W K K Y C L A T S G D T | (SEQ ID No:37) |
| 7. | A0A0F7XYJ8 | E S V W K K H G L A I S G N I | (SEQ ID No:43) |
| | | A N V W K R H C L A T S G D T | (SEQ ID No:49) |
| | | | (SEQ ID No:54) |

SEQUENCE LISTING

```
Sequence total quantity: 66
SEQ ID NO: 1             moltype = DNA    length = 1143
FEATURE                  Location/Qualifiers
source                   1..1143
                         mol_type = genomic DNA
                         organism = Photobacterium phosphoreum
SEQUENCE: 1
atgaccctga gcattgaaaa tcagaacaaa ctggatgaat tctgggccta ttgcgtgaaa   60
aaccagtatt ttaacattgg ctatccggaa agcgcagatt tcgattatac cattctggaa  120
cgttttatgc gcttcagcat taataactgt ggtgattggg cagagtattg caattatctg  180
ctgaacagct tcgacttcga aaaagaagtg atggaatatt ttgccgacct gttcaaaatc  240
ccgtttgaag atagctgggg ttatgttacc aatggtggca ccgaaagcaa tatgtttggt  300
tgttatctgg gtcgtgaact gtttccggat ggcaccctgt attatagcaa agatacccat  360
tattccgtgc caaaattgt taaactgctg cgtattaaaa gccagctggt tgatagcctg  420
ccgaatggtg aaaattgatta tgatgatctg attagcaaaa tcaaacagga cgatgaaaaa  480
cacccgatca tttttgcaaa tattggcacc accgttcgtg gtgcaattga tgatattagt  540
aaaatccagg ccatgattgg tgaactgggt attaaacgtg aggattatta cattcatgca  600
gatgcagcac tgagcggtat gattctgccg tttgttgatg aaccgcaggg ttttaacttt  660
gccgatggta ttgatagcat tggtgttagc ggtcataaaa tgattggtag cccgattccg  720
tgtggtattg ttgttgcaaa aaaacgtaat gtggatgcca ttagcgtgga aatcgattat  780
atcagcgcac acgataaaac cattaccggt agtcgtaatg tcatacacc gctgatgatg  840
tggtgtcag tgaaaagcca tagccatgca gattttaaac gtcgtattaa tcgtagcctg  900
gatctggcac agcatgcagt tcagcgcctg cagaccgcac gtattaatgc atggtgtaac  960
aaaaatagca tcaccgttgt ttttccgtgt ccgagcgaag cagtttggaa aaaacattgt 1020
ctggcaacca gcggtggtca ggcacatctg attaccaccg cacatcatct ggatgcaagc 1080
aaagttgatg cactgattga tgacgttatc aaagatgcaa acggtgaaat gattgcagcc 1140
taa                                                                1143

SEQ ID NO: 2             moltype = DNA    length = 1143
FEATURE                  Location/Qualifiers
misc_feature             1..1143
                         note = DNA having modified codons, which encodes histidine
                          decarboxylase gene derived from Photobacterium phosphoreum
source                   1..1143
                         mol_type = other DNA
                         organism = synthetic construct
SEQUENCE: 2
atgactttat ctattgaaaa ccaaaacaaa ttagacgaat tttgggctta ttgtgttaaa   60
aaccaatatt ttaacattgg ttatcctgaa tctgctgact tgactatac tattttagaa  120
cgttttatgc gttttctat taacaactgt ggtgactggg ctgaatattg taactattta  180
ttaaactctt ttgactttga aaaagaagtg atggaatatt ttgctgactt atttaaaatt  240
ccttttgaag actcttgggg ttatgttact aacggtggta ctgaatctaa catgtttggt  300
tgttatttag gtcgtgaatt atttcctgac ggtactttat attattctaa agacactcat  360
tattctgttg ctaaaattgt taaattatta cgtattaaat ctcaattagt tgactctta  420
cctaacggtg aaattgacta tgacgactta atttctaaaa ttaaacaaga cgacgaaaaa  480
catcctatta tttttgctaa cattggtact actgttcgtg gtgctattga cgacatttct  540
aaaattcaag ctatgattgg tgaattaggt attaaacgtg aagactatta tattcatgct  600
gacgctgctt tatctggtat gattttccct tttgttgacg aacctcaagg ttttaacttt  660
gctgacggta ttgactctat tggtgttct ggtcataaaa tgattggttc tcctattcct  720
tgtggtattg ttgttgctaa aaaacgtaat gttgacgcta tttctgttga aattgactat  780
atttctgctc atgacaaaac tattactggt tctcgtaacg tcatactcc tttaatgatg  840
tggtgtgctg ttaaatctca ttctcatgct gactttaaac gtcgtattaa ccgttcttta  900
gacttagctc aacatgctgt tcaacgttta caaactgctg gtattaacgc ttggtgtaac  960
aaaaactcta ttactgttgt ttttccttgt ccttctgaag ctgttggaa aaaacattgt 1020
ttagctactt ctggtggtca agctcattta attactactg ctcatcattt agacgcttct 1080
aaagttgacg ctttaattga cgacgttatt aaagacgcta acggtgaaat gattgctgct 1140
tga                                                                1143

SEQ ID NO: 3             moltype = AA    length = 380
FEATURE                  Location/Qualifiers
source                   1..380
                         mol_type = protein
                         organism = Photobacterium phosphoreum
SEQUENCE: 3
MTLSIENQNK LDEFWAYCVK NQYFNIGYPE SADFDYTILE RFMRFSINNC GDWAEYCNYL   60
LNSFDFEKEV MEYFADLFKI PFEDSWGYVT NGGTESNMFG CYLGRELFPD GTLYYSKDTH  120
YSVAKIVKLL RIKSQLVDSL PNGEIDYDDL ISKIKQDDEK HPIIFANIGT TVRGAIDDIS  180
KIQAMIGELG IKREDYYIHA DAALSGMILP FVDEPQGFNF ADGIDSIGVS GHKMIGSPIP  240
CGIVVAKKRN VDAISVEIDY ISAHDKTITG SRNGHTPLMM WCAVKSHSHA DFKRRINRSL  300
DLAQHAVQRL QTAGINAWCN KNSITVVFPC PSEAVWKKHC LATSGGQAHL ITTAHHLDAS  360
KVDALIDDVI KDANGEMIAA                                               380

SEQ ID NO: 4             moltype = DNA    length = 26
FEATURE                  Location/Qualifiers
misc_feature             1..26
                         note = primer for amplifying HisDC
source                   1..26
                         mol_type = other DNA
```

```
                            organism = synthetic construct
SEQUENCE: 4
tatcgaaggt cgtcatatga ccaccc                                              26

SEQ ID NO: 5             moltype = DNA   length = 25
FEATURE                  Location/Qualifiers
misc_feature             1..25
                         note = primer for amplifying HisDC
source                   1..25
                         mol_type = other DNA
                         organism = synthetic construct
SEQUENCE: 5
tttgttagca gccggatcct taggc                                               25

SEQ ID NO: 6             moltype = DNA   length = 66
FEATURE                  Location/Qualifiers
misc_feature             1..66
                         note = primer for adding His-tag to 3'-terminus
source                   1..66
                         mol_type = other DNA
                         organism = synthetic construct
SEQUENCE: 6
gccgcactcg agcaccacca ccaccaccac tgaggatccg gctgctaaca aagcccgaaa         60
ggaagc                                                                    66

SEQ ID NO: 7             moltype = DNA   length = 19
FEATURE                  Location/Qualifiers
misc_feature             1..19
                         note = primer for adding His-tag to 3'-terminus
source                   1..19
                         mol_type = other DNA
                         organism = synthetic construct
SEQUENCE: 7
ggctgcaatc atttcaccg                                                      19

SEQ ID NO: 8             moltype = AA   length = 18
FEATURE                  Location/Qualifiers
REGION                   1..18
                         note = HisDC consensus sequence
source                   1..18
                         mol_type = protein
                         organism = synthetic construct
SEQUENCE: 8
CGDWAEYCNY LLNSFDFE                                                       18

SEQ ID NO: 9             moltype = AA   length = 26
FEATURE                  Location/Qualifiers
REGION                   1..26
                         note = HisDC consensus sequence
source                   1..26
                         mol_type = protein
                         organism = synthetic construct
SEQUENCE: 9
SWGYVTNGGT EGNMFGCYLA RELFPD                                              26

SEQ ID NO: 10            moltype = AA   length = 18
FEATURE                  Location/Qualifiers
REGION                   1..18
                         note = HisDC consensus sequence
source                   1..18
                         mol_type = protein
                         organism = synthetic construct
SEQUENCE: 10
IGSRNGHTPL MMWEAIKS                                                       18

SEQ ID NO: 11            moltype = AA   length = 20
FEATURE                  Location/Qualifiers
REGION                   1..20
                         note = HisDC consensus sequence
source                   1..20
                         mol_type = protein
                         organism = synthetic construct
SEQUENCE: 11
RFQAAGINAW RNKNSITVVF                                                     20

SEQ ID NO: 12            moltype = AA   length = 15
FEATURE                  Location/Qualifiers
REGION                   1..15
                         note = HisDC consensus sequence
```

```
source                    1..15
                          mol_type = protein
                          organism = synthetic construct
SEQUENCE: 12
NKNSITVVFP CPSEA                                                          15

SEQ ID NO: 13             moltype = AA  length = 14
FEATURE                   Location/Qualifiers
REGION                    1..14
                          note = HisDC consensus sequence
source                    1..14
                          mol_type = protein
                          organism = synthetic construct
SEQUENCE: 13
EAVWKKHCLA TSGI                                                           14

SEQ ID NO: 14             moltype = AA  length = 18
FEATURE                   Location/Qualifiers
source                    1..18
                          mol_type = protein
                          organism = Photobacterium phosphoreum
SEQUENCE: 14
CGDWAEYCNY LLNSFDFE                                                       18

SEQ ID NO: 15             moltype = AA  length = 25
FEATURE                   Location/Qualifiers
source                    1..25
                          mol_type = protein
                          organism = Photobacterium phosphoreum
SEQUENCE: 15
WGYVTNGGTE SNMFGCYLGR ELFPD                                               25

SEQ ID NO: 16             moltype = AA  length = 18
FEATURE                   Location/Qualifiers
source                    1..18
                          mol_type = protein
                          organism = Photobacterium phosphoreum
SEQUENCE: 16
TGSRNGHTPL MMWCAVKS                                                       18

SEQ ID NO: 17             moltype = AA  length = 19
FEATURE                   Location/Qualifiers
source                    1..19
                          mol_type = protein
                          organism = Photobacterium phosphoreum
SEQUENCE: 17
LQTAGINAWC NKNSITVVF                                                      19

SEQ ID NO: 18             moltype = AA  length = 14
FEATURE                   Location/Qualifiers
source                    1..14
                          mol_type = protein
                          organism = Photobacterium phosphoreum
SEQUENCE: 18
KNSITVVFPC PSEA                                                           14

SEQ ID NO: 19             moltype = AA  length = 15
FEATURE                   Location/Qualifiers
source                    1..15
                          mol_type = protein
                          organism = Photobacterium phosphoreum
SEQUENCE: 19
EAVWKKHCLA TSGGQ                                                          15

SEQ ID NO: 20             moltype = AA  length = 18
FEATURE                   Location/Qualifiers
source                    1..18
                          mol_type = protein
                          organism = Serratia rubidaea
SEQUENCE: 20
CGDWSEYCNY LLNSFEFE                                                       18

SEQ ID NO: 21             moltype = AA  length = 25
FEATURE                   Location/Qualifiers
source                    1..25
                          mol_type = protein
                          organism = Serratia rubidaea
SEQUENCE: 21
WGYVTNGGTE SNMFGCYLGR EIFPD                                               25
```

```
SEQ ID NO: 22             moltype = AA  length = 18
FEATURE                   Location/Qualifiers
source                    1..18
                          mol_type = protein
                          organism = Serratia rubidaea
SEQUENCE: 22
TGSRNGHTPM MMWEAIKS                                                 18

SEQ ID NO: 23             moltype = AA  length = 19
FEATURE                   Location/Qualifiers
source                    1..19
                          mol_type = protein
                          organism = Serratia rubidaea
SEQUENCE: 23
LQSAGVNAWR NKNSITVVF                                                19

SEQ ID NO: 24             moltype = AA  length = 14
FEATURE                   Location/Qualifiers
source                    1..14
                          mol_type = protein
                          organism = Serratia rubidaea
SEQUENCE: 24
KNSITVVFPC PSEA                                                     14

SEQ ID NO: 25             moltype = AA  length = 15
FEATURE                   Location/Qualifiers
source                    1..15
                          mol_type = protein
                          organism = Serratia rubidaea
SEQUENCE: 25
EAVWKKHCLA TSGEV                                                    15

SEQ ID NO: 26             moltype = AA  length = 18
FEATURE                   Location/Qualifiers
source                    1..18
                          mol_type = protein
                          organism = Klebsiella planticola
SEQUENCE: 26
CGDWGEYCNY LLNSFDFE                                                 18

SEQ ID NO: 27             moltype = AA  length = 25
FEATURE                   Location/Qualifiers
source                    1..25
                          mol_type = protein
                          organism = Klebsiella planticola
SEQUENCE: 27
WGYVTNGGTE GNMFGCYLSR EIFPN                                         25

SEQ ID NO: 28             moltype = AA  length = 18
FEATURE                   Location/Qualifiers
source                    1..18
                          mol_type = protein
                          organism = Klebsiella planticola
SEQUENCE: 28
SGSRNGHTPL MMWEAIRS                                                 18

SEQ ID NO: 29             moltype = AA  length = 19
FEATURE                   Location/Qualifiers
source                    1..19
                          mol_type = protein
                          organism = Klebsiella planticola
SEQUENCE: 29
FQSAGIDAWR NKNSITVVF                                                19

SEQ ID NO: 30             moltype = AA  length = 14
FEATURE                   Location/Qualifiers
source                    1..14
                          mol_type = protein
                          organism = Klebsiella planticola
SEQUENCE: 30
KNSITVVFPC PSEA                                                     14

SEQ ID NO: 31             moltype = AA  length = 15
FEATURE                   Location/Qualifiers
source                    1..15
                          mol_type = protein
                          organism = Klebsiella planticola
SEQUENCE: 31
```

```
EAVWKKHCLA TSGDI                                                              15

SEQ ID NO: 32            moltype = AA  length = 18
FEATURE                  Location/Qualifiers
source                   1..18
                         mol_type = protein
                         organism = Photobacterium damselae
SEQUENCE: 32
CGDWSEYCNY LLNSFDFE                                                           18

SEQ ID NO: 33            moltype = AA  length = 25
FEATURE                  Location/Qualifiers
source                   1..25
                         mol_type = protein
                         organism = Photobacterium damselae
SEQUENCE: 33
WGYVTNGGTE GNMFGCYLAR ELFPD                                                   25

SEQ ID NO: 34            moltype = AA  length = 18
FEATURE                  Location/Qualifiers
source                   1..18
                         mol_type = protein
                         organism = Photobacterium damselae
SEQUENCE: 34
TGSRNGHTPL MMWEAVKS                                                           18

SEQ ID NO: 35            moltype = AA  length = 19
FEATURE                  Location/Qualifiers
source                   1..19
                         mol_type = protein
                         organism = Photobacterium damselae
SEQUENCE: 35
FQKAGIDAWR NKNSITVVF                                                          19

SEQ ID NO: 36            moltype = AA  length = 14
FEATURE                  Location/Qualifiers
source                   1..14
                         mol_type = protein
                         organism = Photobacterium damselae
SEQUENCE: 36
KNSITVVFPC PSED                                                               14

SEQ ID NO: 37            moltype = AA  length = 15
FEATURE                  Location/Qualifiers
source                   1..15
                         mol_type = protein
                         organism = Photobacterium damselae
SEQUENCE: 37
EDVWKKHCLA TSNGL                                                              15

SEQ ID NO: 38            moltype = AA  length = 18
FEATURE                  Location/Qualifiers
source                   1..18
                         mol_type = protein
                         organism = Xenorhabdus poinarii
SEQUENCE: 38
CGDWGAECNY LLNSFEFE                                                           18

SEQ ID NO: 39            moltype = AA  length = 25
FEATURE                  Location/Qualifiers
source                   1..25
                         mol_type = protein
                         organism = Xenorhabdus poinarii
SEQUENCE: 39
WGYVTNGGTE GNMFGCYLGR ELFPD                                                   25

SEQ ID NO: 40            moltype = AA  length = 18
FEATURE                  Location/Qualifiers
source                   1..18
                         mol_type = protein
                         organism = Xenorhabdus poinarii
SEQUENCE: 40
SGSRNGQTPL MMWAAIRS                                                           18

SEQ ID NO: 41            moltype = AA  length = 19
FEATURE                  Location/Qualifiers
source                   1..19
                         mol_type = protein
                         organism = Xenorhabdus poinarii
```

```
SEQUENCE: 41
FRAAGINAWR HDNSITVVF                                                              19

SEQ ID NO: 42           moltype = AA  length = 14
FEATURE                 Location/Qualifiers
source                  1..14
                        mol_type = protein
                        organism = Xenorhabdus poinarii
SEQUENCE: 42
DNSITVVFPC PSVA                                                                   14

SEQ ID NO: 43           moltype = AA  length = 15
FEATURE                 Location/Qualifiers
source                  1..15
                        mol_type = protein
                        organism = Xenorhabdus poinarii
SEQUENCE: 43
VAVWKKYCLA TSGDT                                                                  15

SEQ ID NO: 44           moltype = AA  length = 18
FEATURE                 Location/Qualifiers
source                  1..18
                        mol_type = protein
                        organism = Klebsiella pneumoniae
SEQUENCE: 44
CGDWADYCNY RLNTFDFE                                                               18

SEQ ID NO: 45           moltype = AA  length = 25
FEATURE                 Location/Qualifiers
source                  1..25
                        mol_type = protein
                        organism = Klebsiella pneumoniae
SEQUENCE: 45
WGYVTNGGTE GNMFGCYLGR ELFPD                                                       25

SEQ ID NO: 46           moltype = AA  length = 18
FEATURE                 Location/Qualifiers
source                  1..18
                        mol_type = protein
                        organism = Klebsiella pneumoniae
SEQUENCE: 46
TGSRNGHTPL IMWEAIRS                                                               18

SEQ ID NO: 47           moltype = AA  length = 19
FEATURE                 Location/Qualifiers
source                  1..19
                        mol_type = protein
                        organism = Klebsiella pneumoniae
SEQUENCE: 47
FQKAGINAWR NKNSITVIF                                                              19

SEQ ID NO: 48           moltype = AA  length = 14
FEATURE                 Location/Qualifiers
source                  1..14
                        mol_type = protein
                        organism = Klebsiella pneumoniae
SEQUENCE: 48
KNSITVIFPC PSES                                                                   14

SEQ ID NO: 49           moltype = AA  length = 15
FEATURE                 Location/Qualifiers
source                  1..15
                        mol_type = protein
                        organism = Klebsiella pneumoniae
SEQUENCE: 49
ESVWKKHGLA ISGNI                                                                  15

SEQ ID NO: 50           moltype = AA  length = 25
FEATURE                 Location/Qualifiers
source                  1..25
                        mol_type = protein
                        organism = Pseudomonas sp.
SEQUENCE: 50
WGYVTNGGTE GNMFGCYLAR ELFPD                                                       25

SEQ ID NO: 51           moltype = AA  length = 18
FEATURE                 Location/Qualifiers
source                  1..18
                        mol_type = protein
```

```
                              organism = Pseudomonas sp.
SEQUENCE: 51
SGSRNGHTPL MMWAALRS                                                  18

SEQ ID NO: 52          moltype = AA  length = 19
FEATURE                Location/Qualifiers
source                 1..19
                       mol_type = protein
                       organism = Pseudomonas sp.
SEQUENCE: 52
LRAAGIDAWR NPNSITVVF                                                 19

SEQ ID NO: 53          moltype = AA  length = 14
FEATURE                Location/Qualifiers
source                 1..14
                       mol_type = protein
                       organism = Pseudomonas sp.
SEQUENCE: 53
PNSITVVFPC PSAN                                                      14

SEQ ID NO: 54          moltype = AA  length = 15
FEATURE                Location/Qualifiers
source                 1..15
                       mol_type = protein
                       organism = Pseudomonas sp.
SEQUENCE: 54
ANVWKRHCLA TSGDT                                                     15

SEQ ID NO: 55          moltype = AA  length = 25
FEATURE                Location/Qualifiers
source                 1..25
                       mol_type = protein
                       organism = Chromobacterium sp.
SEQUENCE: 55
WGYVTNGGTE GNMFGCYLAR ELFPD                                          25

SEQ ID NO: 56          moltype = AA  length = 19
FEATURE                Location/Qualifiers
source                 1..19
                       mol_type = protein
                       organism = Chromobacterium sp.
SEQUENCE: 56
FQAAGIQAWR CKNSITVVF                                                 19

SEQ ID NO: 57          moltype = AA  length = 14
FEATURE                Location/Qualifiers
source                 1..14
                       mol_type = protein
                       organism = Chromobacterium sp.
SEQUENCE: 57
KNSITVVFPS PSEP                                                      14

SEQ ID NO: 58          moltype = AA  length = 25
FEATURE                Location/Qualifiers
source                 1..25
                       mol_type = protein
                       organism = Aeromonas salmonicida
SEQUENCE: 58
WGYVTNGGTE GNMFGCYLAR ELFPE                                          25

SEQ ID NO: 59          moltype = AA  length = 19
FEATURE                Location/Qualifiers
source                 1..19
                       mol_type = protein
                       organism = Aeromonas salmonicida
SEQUENCE: 59
FHAKGIHAWR NPNSITVVF                                                 19

SEQ ID NO: 60          moltype = AA  length = 14
FEATURE                Location/Qualifiers
source                 1..14
                       mol_type = protein
                       organism = Aeromonas salmonicida
SEQUENCE: 60
PNSITVVFPK PADH                                                      14

SEQ ID NO: 61          moltype = AA  length = 25
FEATURE                Location/Qualifiers
source                 1..25
```

```
                        mol_type = protein
                        organism = Vibrio nigripulchritudo
SEQUENCE: 61
WGYVTNGGTE GNMYSCYLAR ELFPN                                         25

SEQ ID NO: 62           moltype = AA  length = 19
FEATURE                 Location/Qualifiers
source                  1..19
                        mol_type = protein
                        organism = Vibrio nigripulchritudo
SEQUENCE: 62
LKSKGVPAWL NPNSVIVVF                                                19

SEQ ID NO: 63           moltype = AA  length = 14
FEATURE                 Location/Qualifiers
source                  1..14
                        mol_type = protein
                        organism = Vibrio nigripulchritudo
SEQUENCE: 63
PNSVIVVFPT PTEA                                                     14

SEQ ID NO: 64           moltype = AA  length = 25
FEATURE                 Location/Qualifiers
source                  1..25
                        mol_type = protein
                        organism = Vibrio neptunius
SEQUENCE: 64
WGYVTNGGTE GNMYGCYLAR ERFPD                                         25

SEQ ID NO: 65           moltype = AA  length = 25
FEATURE                 Location/Qualifiers
source                  1..25
                        mol_type = protein
                        organism = Vibrio coralliilyticus
SEQUENCE: 65
WGYVTNGGTE GNMYGCYLAR ERFPD                                         25

SEQ ID NO: 66           moltype = AA  length = 25
FEATURE                 Location/Qualifiers
source                  1..25
                        mol_type = protein
                        organism = Oligella urethralis
SEQUENCE: 66
WGYFTSGSTE SNLFGCYLAR ERFKN                                         25
```

MUTATED HISTIDINE DECARBOXYLASE AND USE THEREOF

This application is a Divisional of, and claims priority under 35 U.S.C. § 120 to U.S. patent application Ser. No. 16/566,236, filed Sep. 10, 2019, U.S. Pat. No. 11,713,454, which was a Continuation of, and claims priority under 35 U.S.C. § 120 to, International Application No. PCT/JP2018/009572, filed Mar. 12, 2018 and claims priority therethrough under 35 U.S.C. § 119 to Japanese Patent Application No. 2017-047813, filed Mar. 13, 2017, the entireties of which are incorporated by reference herein. Also, the Sequence Listing filed electronically on Feb. 17, 2023 is hereby incorporated by reference (File name: 2023-02-17T_US-598D_SEQ_LIST; File size: 63 KB; Date recorded: Feb. 9, 2023).

TECHNICAL FIELD

The present invention relates to a mutated histidine decarboxylase and the use thereof.

BACKGROUND ART

Histidine is known to be a biomarker of Crohn's disease, inflammatory bowel diseases such as ulcerative colitis, histidinemia, cardiac cachexia, cancer, and lifestyle diseases (for example, WO 2016/056631; Levy H (2004) "Histidinemia" Orphanet; Kawai Y, et al. "Molecular characterization of histidinemia: identification of four missense mutations in the histidase gene" Hum Genet. 116, 340-346, 2005; "Saishin Rinsho kensa koumoku jiten" (The latest Clinical inspection items encyclopedia) supervised by Ikunosuke Sakurabayashi and Kazunari Kumasaka (2008) Ishiyaku Pub, Inc., pp. 205; Hisamatsu T, et al. PLoS One. 2012; 7(1): e31131; and Miyagi Y, et al. PLoS One. 2011; 6(9): e24143). Known examples of methods for measuring amino acids include methods using instruments such as an amino acid analyzer, a high-performance liquid chromatography (HPLC), and an LC-MS, as well as a fluorescence analysis method (for example, Japanese Patent Application Laid-open No. 2001-242174) and a method using a galactose oxidase (for example, Hasebe Y, et al. Sensors and Actuators B 66 (2000) 12-15).

SUMMARY

However, the instruments used in the above-mentioned methods are designed for large-scale production and are expensive; furthermore, expert knowledge and proficiency are required for maintenance and operation of these instruments, increasing the costs for introduction, maintenance, and use. In addition, in principle, samples are required to be analyzed sequentially, and therefore, it can take a long time to analyze many samples.

The enzyme histidine decarboxylase functions to generate histamine by acting on histidine, and practical implementation of this function for measuring histidine has been explored. To this end, the activity and stabilities, such as, for example, thermal stability, storage stability, and oxidation resistance, of the enzyme would have to be improved and increased for practical implementation.

It is therefore, an aspect of the present invention to provide a mutated histidine decarboxylase suitable for practical implementation.

It is an aspect of the present invention to provide a mutated histidine decarboxylase, wherein said mutated histidine decarboxylase comprises a motif selected from the group consisting of: A) Motif (1): $GDWX_1X_2X_3CNYX_4$ motif, where $X_1$ represents A, S, or G; $X_2$ represents E, A, or D; $X_3$ represents Y or E, and $X_4$ represents L or R; B) Motif (2): $EXSNX_6X_7X_8CYLX_9$ motif, where $X_5$ represents S or G, $X_6$ represents M or L, $X_7$ represents F or Y, $X_8$ represents G or S, and $X_9$ represents G, S, or A; C) Motif (3): $GSRNGX_{10}TPX_{11}X_{12}MWX_{13}AX_{14}X_{15}S$ motif, where $X_{10}$ represents H or Q, $X_{11}$ represents L or M, $X_{12}$ represents M or I, $X_{13}$ represents C, E or A, $X_{14}$ represents V or I, and $X_{15}$ represents K or R; D) Motif (4): $GX_{16}X_{17}AWX_{18}X_{19}$ motif, where $X_{16}$ represents I or V, $X_{17}$ represents N, D, Q, H, or P, $X_{18}$ represents C, R, or L, and $X_{19}$ represents N, H, or C; E) Motif (5): $TVX_{20}FPCPSX_{21}X_{22}$ motif, where $X_{20}$ represents V or I, $X_{21}$ represents E, V, or A, and $X_{22}$ represents A, D, S, or N; and F) Motif (6): $VWKX_{23}X_{24}CLAX_{25}S$ motif, where $X_{23}$ represents K or R, $X_{24}$ represents H or Y, and $X_{25}$ represents T or I; and G) combinations thereof; wherein at least one amino acid in at least one of Motifs (1) to (6) is mutated as compared to a wild-type histidine decarboxylase; wherein said mutated histidine has higher histidine decarboxylase activity and/or stability than a wild-type histidine decarboxylase.

It is a further aspect of the present invention to provide the mutated histidine decarboxylase as described above, wherein the at least one amino acid residue is selected from the group consisting of a sulfur-containing amino acid residue, an aromatic amino acid residue, an acidic amino acid residue, a hydroxy group-containing amino acid residue, an amide group-containing amino acid residue, a branched chain amino acid residue, and combinations thereof.

It is a further aspect of the present invention to provide the mutated histidine decarboxylase as described above, wherein the sulfur-containing amino acid residue is selected from the group consisting of cysteine, methionine, and combinations thereof; the aromatic amino acid residue is selected from the group consisting of tryptophan, phenylalanine, histidine, tyrosine, and combinations thereof; the acidic amino acid residue is selected from the group consisting of glutamic acid, aspartic acid, and combinations thereof; the hydroxy group-containing amino residue acid is selected from the group consisting of serine, threonine, and combinations thereof; the amide group-containing amino acid residue is selected from the group consisting of asparagine, glutamine, and combinations thereof; and the branched chain amino acid residue is selected from the group consisting of valine, leucine, isoleucine, and combinations thereof.

It is a further aspect of the present invention to provide the mutated histidine decarboxylase as described above, wherein the sulfur-containing amino acid residue is substituted with an amino acid residue selected from the group consisting of alanine, glycine, serine, threonine, arginine, lysine, histidine, isoleucine, leucine, and valine; the aromatic amino acid residue is substituted with an amino acid residue selected from the group consisting of phenylalanine, tyrosine, tryptophan, histidine, asparagine, glutamine, lysine, and arginine; the acidic amino acid residue is substituted with a serine or threonine; the hydroxy group-containing amino acid residue is substituted with a glycine or alanine; the amide group-containing amino acid residue is substituted with an amino acid residue selected from the group consisting of phenylalanine, tyrosine, tryptophan, histidine, arginine, lysine, serine, and threonine; and the branched chain amino acid residue is substituted with an amino acid residue selected from the group consisting of isoleucine, leucine, and methionine.

It is further aspect of the present invention to provide the mutated histidine decarboxylase as described above, wherein the at least one amino acid residue is mutated to have a mutation selected from the group consisting of: a) mutation of at least one amino acid residue in the CNY motif in Motif (1); b) mutation of $X_2$ in Motif (1); c) mutation of at least one amino acid residue in the CYL motif in Motif (2); d) mutation of $X_5$ in Motif (2); e) mutation of $X_6$ in Motif (2); f) mutation of $X_{12}$ in Motif (3); g) mutation of M in Motif (3); h) mutation of $X_{13}$ in Motif (3); i) mutation of $X_{18}$ in Motif (4); j) mutation of $X_{20}$ in Motif (5); k) mutation of at least one amino acid residue in the FPCPS motif in Motif (5); l) mutation of at least one amino acid residue in the CLATS motif in Motif (6); and combinations thereof.

It is a further aspect of the present invention to provide the mutated histidine decarboxylase as described above, wherein at least one amino acid residue is selected from the group consisting of: a) the C in the CNY motif in Motif (1), b) the C in the CYL motif in Motif (2), c) the C in the FPCPS motif in Motif (5), and d) the C in the CLATS motif in Motif (6).

It is a further aspect of the present invention to provide the mutated histidine decarboxylase as described above, wherein the at least one amino acid residue is mutated to have a mutation selected from the group consisting of: a) substitution of the C in the CNY motif in Motif (1) with alanine, serine, threonine, arginine, or glycine; b) substitution of $X_2$ in Motif (1) with serine; c) substitution of the C in the CYL motif in Motif (2) with alanine, serine, or valine; d) substitution of the Y in the CYL motif in Motif (2) with phenylalanine; e) substitution of $X_5$ in Motif (2) with glycine; f) substitution of $X_6$ in Motif (2) with valine; g) substitution of $X_{12}$ in Motif (3) with isoleucine; h) substitution of M in Motif (3) with leucine or isoleucine; i) substitution of $X_{13}$ in Motif (3) with alanine, serine, or valine; j) substitution of $X_{18}$ in Motif (4) with alanine, serine, or valine; k) substitution of $X_{20}$ in Motif (5) with isoleucine; l) substitution of the C in the FPCPS motif in Motif (5) with alanine, serine, or valine; m) substitution of the C in the CLATS motif in Motif (6) with alanine, serine, or valine; and n) combinations thereof.

It is a further aspect of the present invention to provide the mutated histidine decarboxylase as described above, wherein the wild-type histidine decarboxylase is selected from the group consisting of: (a) an amino acid sequence of SEQ ID No: 3; (b) the amino acid sequence of SEQ ID No. 3, but wherein one or several amino acid residues in the amino acid sequence are substituted, deleted, inserted, or added; and (c) an amino acid sequence that is 90% or more identical to the amino acid sequence of SEQ ID No: 3.

It is a further aspect of the present invention to provide a mutated histidine decarboxylase, wherein said mutated histidine decarboxylase comprises a mutation as compared to a wild-type histidine decarboxylase of an amino acid residue selected from the group consisting of: a) mutation of tryptophan at position 15; b) mutation of asparagine at position 21; c) mutation of glutamine at position 22; d) mutation of methionine at position 43; e) mutation of glutamic acid at position 55; f) mutation of cysteine at position 57; g) mutation of serine at position 96; h) mutation of methionine at position 98; i) mutation of cysteine at position 101; j) mutation of tyrosine at position 102; k) mutation of tyrosine at position 114; l) mutation of leucine at position 130; m) mutation of isoleucine at position 132; n) mutation of tyrosine at position 147; o) mutation of methionine at position 185; p) mutation of tyrosine at position 196; q) mutation of methionine at position 234; r) mutation of methionine at position 279; s) mutation of methionine at position 280; t) mutation of cysteine at position 282; u) mutation of cysteine at position 319; v) mutation of valine at position 327; w) mutation of cysteine at position 330; x) mutation of cysteine at position 340; and y) mutation of methionine at position 377; and z) combinations thereof; wherein the wild-type histidine decarboxylase is selected from the group consisting of: (i) an amino acid sequence of SEQ ID No: 3; (ii) an amino acid sequence in which one or several amino acid residues in the amino acid sequence of SEQ ID No: 3 are substituted, deleted, inserted or added; and (iii) an amino acid sequence which is 90% or more is identical to the amino acid sequence of SEQ ID No: 3; wherein the mutated histidine decarboxylase has higher histidine decarboxylase activity and/or stability than the wild-type histidine decarboxylase.

It is a further aspect of the present invention to provide the mutated histidine decarboxylase as described above, wherein said mutation is selected from the group consisting of following: a) substitution of tryptophan at position 15 with phenylalanine; b) mutation of asparagine at position 21 with histidine; c) mutation of glutamine at position 22 with arginine; d) mutation of methionine at position 43 with leucine; e) mutation of glutamic acid at position 55 with serine; f) mutation of cysteine at position 57 with alanine, glycine, arginine, serine, or threonine; g) mutation of serine at position 96 with glycine; h) mutation of methionine at position 98 with valine; i) mutation of cysteine at position 101 with alanine, serine, or valine; j) mutation of tyrosine at position 102 with phenylalanine; k) mutation of tyrosine at position 114 with phenylalanine; l) mutation of leucine at position 130 with isoleucine; m) mutation of isoleucine at position 132 with leucine or methionine; n) mutation of tyrosine at position 147 with phenylalanine; o) mutation of methionine at position 185 with threonine, leucine, isoleucine, serine, or alanine; p) mutation of tyrosine at position 196 with phenylalanine; q) mutation of methionine at position 234 with alanine; r) mutation of methionine at position 279 with isoleucine; s) mutation of methionine at position 280 with leucine or isoleucine; t) mutation of cysteine at position 282 with alanine, serine, or valine; u) mutation of cysteine at position 319 with alanine, serine, or valine; v) mutation of valine at position 327 with isoleucine; w) mutation of cysteine at position 330 with alanine, serine, or valine; x) mutation of cysteine at position 340 with alanine; y) mutation of methionine at position 377 with threonine, leucine, isoleucine, or alanine; and z) combinations thereof.

It is a further aspect of the present invention to provide the mutated histidine decarboxylase as described above, wherein the stability is selected from the group consisting of thermal stability, storage stability, oxidation resistance, and combinations thereof.

It is a further aspect of the present invention to provide a polynucleotide encoding the decarboxylase as described above.

It is a further aspect of the present invention to provide an expression vector comprising the polynucleotide as described above.

It is a further aspect of the present invention to provide a transformant comprising the expression vector as described above.

It is a further aspect of the present invention to provide a kit for analyzing histidine, comprising the mutated histidine decarboxylase as described above.

It is a further aspect of the present invention to provide the kit for analyzing histidine as described above, further comprising a 4-imidazolyl acetaldehyde generating enzyme.

It is a further aspect of the present invention to provide the kit as described above, further comprising a buffer solution or a buffering salt for reaction, a 4-imidazolyl acetaldehyde detecting reagent, a hydrogen peroxide detecting reagent, an ammonia detecting reagent, and/or a reduced type electron donor reagent.

It is a further aspect of the present invention to provide a system for analyzing histidine, comprising the mutated histidine decarboxylase as described above It is a further aspect of the present invention to provide a method for diagnosing ulcerative colitis, cardiac cachexia, lifestyle diseases, cancer, or histidinemia in a subject, comprising a) measuring the amount of histidine in a specimen from the subject using the mutated histidine decarboxylase as described above; b) diagnosing the subject with ulcerative colitis, cardiac cachexia, lifestyle diseases, or cancer when the amount of histidine is lower than a standard amount; and c) diagnosing the subject with histidinemia when the amount of histidine is higher than the standard amount.

It is a further aspect of the present invention to provide a method for determining the risk of recurrence of an inflammatory bowel disease in a subject in remission of an inflammatory bowel disease comprising: a) measuring a histidine amount in a specimen from the subject using the mutated histidine decarboxylase as described above, b) determining that when the amount of histidine is lower than a standard amount, the subject has a high of recurrence of an inflammatory bowel disease, and c) determining that when the amount of histidine is higher than the standard amount, the subject has a low risk of recurrence of an inflammatory bowel disease.

The present invention provides a mutated histidine decarboxylase having improved activity and stabilities, for example, thermal stability, storage stability, and oxidation resistance, and the like, as compared with a wild-type histidine decarboxylase. Such an enzyme is useful for quick and highly sensitive measurements of histidine and/or for production of histamine.

BRIEF DESCRIPTION OF DRAWINGS

FIG. 1 shows an alignment of amino acid sequences near Motif (1) of a histidine decarboxylase derived from *Photobacterium phosphoreum* (this enzyme is designated "HisDC", and is shown as residues 50-67 of SEQ ID No. 3) and of histidine decarboxylases derived from other organisms (indicated by UniProt accession Nos.).

FIG. 2 shows an alignment of amino acid sequences near Motif (2) of a histidine decarboxylase derived from *Photobacterium phosphoreum* (this enzyme is designated "HisDC", and is shown as residues 85-110 of SEQ ID No. 3) and of histidine decarboxylases derived from other organisms (indicated by UniProt accession Nos.).

FIG. 3 shows an alignment of amino acid sequences near Motif (3) of a histidine decarboxylase derived from *Photobacterium phosphoreum* (this enzyme is designated "HisDC", and is shown as residues 269-286 of SEQ ID No. 3) and of histidine decarboxylases derived from other organisms (indicated by UniProt accession Nos.).

FIG. 4 shows an alignment of amino acid sequences near Motif (4) of a histidine decarboxylase derived from *Photobacterium phosphoreum* (this enzyme is designated "HisDC", and is shown as residues 310-328 of SEQ ID No. 3) and of histidine decarboxylases derived from other organisms (indicated by UniProt accession Nos.).

FIG. 5 shows an alignment of amino acid sequences near Motif (5) of a histidine decarboxylase derived from *Photobacterium phosphoreum* (this enzyme is designated "HisDC", and is shown as residues 321-334 of SEQ ID No. 3) and of histidine decarboxylases derived from other organisms (indicated by UniProt accession Nos.).

FIG. 6 shows an alignment of amino acid sequences near Motif (6) of a histidine decarboxylase derived from *Photobacterium phosphoreum* (this enzyme is designated "HisDC", and is shown as residues 333-347 in SEQ ID No. 3) and of histidine decarboxylases derived from other organisms (indicated by UniProt accession Nos.).

DETAILED DESCRIPTION

Figure 7:
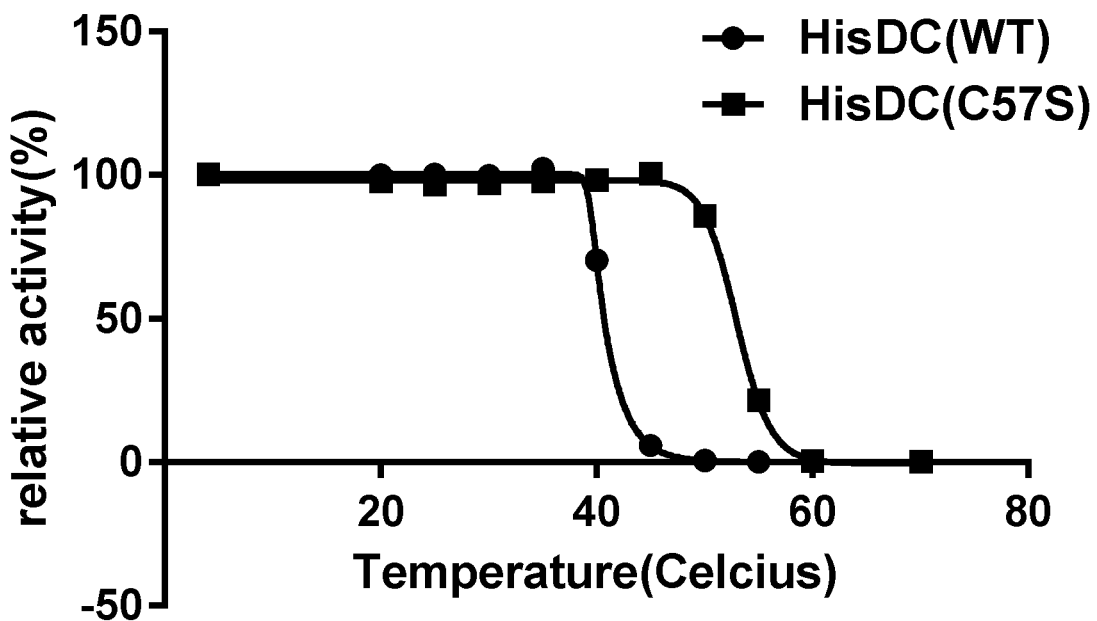
FIG. 7 shows the relative activities of the wild-type HisDC and the C57S mutant after heat treatment at each temperature in Example 6, indicating thermal stability.

Histidine decarboxylase (HisDC: EC 4.1.1.22) is an enzyme that transforms histidine into histamine. The mutated histidine decarboxylase as described herein is a histidine decarboxylase having at least one mutation (mutated) in the wild-type histidine decarboxylase. The mutated histidine decarboxylase has a histidine decarboxylase activity. The histidine decarboxylase activity is an enzyme activity involved in the reaction that transforms histidine to histamine.

The wild-type histidine decarboxylase is used to produce the mutated histidine decarboxylase, and hence is the histidine decarboxylase before being mutated. The wild-type histidine decarboxylase may be derived from various organisms, for example, microorganisms such as bacteria, actinomycetes, and fungi, as well as insects, fishes, animals, and plants, or may be an enzyme protein obtained by expressing a gene that encodes a protein having the above motif by using, as a host, a different organism, for example, *Escherichia coli*, that does not inherently have this gene. Illustrative examples of wild-type histidine decarboxylases include histidine decarboxylases derived from bacteria such as: Photobacterium bacteria (for example, *Photobacterium phosphoreum* and *Photobacterium damselae*), Serratia bacteria (for example, *Serratia rubidaea*), Xenorhabdus bacteria (for example, *Xenorhabdus poinarii*), Morganella bacteria (for example *Morganella morganii*), Klebsiella bacteria (for example, *Klebsiella pneumoniae* and *Klebsiella oxytoca*), Pseudomonas bacteria (for example, *Pseudomonas* sp.), Chromobacterium bacteria (for example, *Chromobacterium* sp.), Aeromonas bacteria (for example, *Aeromonas salmonicida*), Vibrio bacteria (for example, *Vibrio nigripulchritudo, Vibrio neptunius,* and *Vibrio coralliilyticus*), Oligella bacteria (for example, *Oligella urethralis*), Acaryochloris bacteria (for example, *Acaryochloris marina*), Flavobacterium bacteria (for example, *Flavobacterium columnare*), Zobellia bacteria (for example, *Zobellia galactonivorans*), Streptococcus bacteria (for example, Streptococcus thermophiles), Lactobacillus bacteria (for example, Lactobacillus 30a, Lactobacillus saerimneri, Lactobacillus hilgardii, and Lactobacillus buchneri), Oenococcus bacteria (for example, Oenococcus oeni), Tetragenococcus bacteria (for example, Tetragenococcus muriaticus, Tetragenococcus halophilus, etc.), Clostridium bacteria (for example, Clostridium perfringens etc.), Micrococcus bacteria (for example, Micrococcus sp. etc.), Staphylococcus bacteria (for example, Staphylococcus capitis etc.), Raoultella bacteria (for example, Raoultella planticola (Klebsiella planticola) etc.), and Enterobacter bacteria (for example, Enterobacter aerogenes) (Molecular Microbiology (2011) 79(4), 861-871; J. Appl. Microbiol. 2008 104(1): 194-203). Among these bacteria, the Photobacterium bacteria are a particular example, and Photobacterium phosphoreum is also a particular example.

The mutated histidine decarboxylase is, as described above, an enzyme in which at least one amino acid residue of the wild-type histidine decarboxylase is mutated. Examples of the at least one mutation include deletion of an amino acid residue, substitution to another amino acid residue, and addition and insertion of another amino acid residue; and among these mutations, substitution to other amino acid residue is a particular example. Examples of the mutated amino acid residue include at least a sulfur-containing amino acid residue, an aromatic amino acid residue, an acidic amino acid residue, a hydroxy group-containing amino acid residue, an amide group-containing amino acid residue, and/or a branched chain amino acid residue. The sulfur-containing amino acid residue includes a sulfur atom in the structure thereof; and usually includes a sulfur-containing side chain. Illustrative examples thereof include cysteine and methionine. The aromatic amino acid residue includes an aromatic ring or a heterocyclic ring in the structure thereof. Illustrative examples thereof include tryptophan, tyrosine, phenylalanine, and histidine; and among these residues, tryptophan and tyrosine are particular examples. The acidic amino acid residue includes an acidic group in the structure thereof. Illustrative examples thereof include aspartic acid and glutamic acid; and among these residues, glutamic acid is a particular example. The hydroxy group-containing amino acid residue includes a hydroxy group in the structure thereof. Illustrative examples thereof include serine and threonine; and among these residues, serine is a particular example. The amide group-containing amino acid residue includes a primary amide group in the structure thereof; and illustrative examples thereof include asparagine and glutamine. The branched chain amino acid residue includes a branched chain in the structure thereof; and illustrative examples thereof include valine, leucine, and isoleucine.

Although the type of mutation in the sulfur-containing amino acid residue is not particularly restricted, a particular example is the substitution with another amino acid residue, for example, any of alanine, glycine, serine, threonine, arginine, lysine, histidine, isoleucine, leucine, and valine; while substitution with any of alanine, serine, threonine, arginine, glycine, isoleucine, leucine, and valine is a particular example. Cysteine can be substituted with alanine, serine, threonine, arginine, glycine, or valine. Methionine can be substituted with leucine, valine, threonine, isoleucine, serine, or alanine.

Although the type of mutation in the aromatic amino acid residue is not particularly restricted, substitution with another amino acid residue, for example, any of phenylalanine, tyrosine, tryptophan, histidine, asparagine, glutamine, lysine, and arginine is a particular example; while substitution with any of phenylalanine, asparagine, and lysine is a particular example. Tryptophan can be substituted with phenylalanine. Tyrosine can be substituted with phenylalanine. It is known that substitution of tryptophan and tyrosine with asparagine or lysine can increase oxidation resistance of proteins. Accordingly, one would expect that mutation of tryptophan and tyrosine can increase the stability. The aromatic amino acid residue can be substituted with any of phenylalanine, asparagine, and lysine. Here, when substituting with phenylalanine, the aromatic amino acid residue before the mutation can be a residue other than phenylalanine, for example, tryptophan, tyrosine, or histidine, while tryptophan is a particular example.

Although the type of mutation of the acidic amino acid residue is not particularly restricted, substitution with another amino acid residue, for example, with serine and threonine is a particular example, while substitution with serine is another particular example. Glutamic acid can also be substituted with serine.

Although the type of mutation of the hydroxy group-containing amino acid residue is not particularly restricted, substitution with another amino acid residue, for example, with glycine and alanine is a particular example, while substitution with glycine is another particular example. Serine can also be substituted with glycine.

Although the type of mutation of the amide group-containing amino acid residue is not particularly restricted, substitution with another amino acid residue, for example, with any of phenylalanine, tyrosine, tryptophan, histidine, arginine, lysine, serine, and threonine is a particular example, while substitution with any of histidine, arginine, and serine is another particular example. Asparagine can be substituted with histidine, and glutamine with arginine.

Although the type of mutation of the branched chain amino acid residue is not particularly restricted, substitution with another amino acid residue, for example, with any of another branched chain amino acid residue, for example, isoleucine, leucine, and valine, and with methionine is a particular example, while substitution with any of isoleucine, leucine, and methionine is another particular example. Valine can be substituted with isoleucine, leucine with isoleucine, and isoleucine with leucine or methionine.

Examples of the wild-type histidine decarboxylase include a wild-type histidine decarboxylase having at least one motif of the following Motif (1) to Motif (6); a particular example is a wild-type histidine decarboxylase having at least one motif of the following Motifs (1), (2), (5), and (6). Such a decarboxylase can have one motif of Motifs (1), (2), (5), and (6), or a combination of two or more motifs, or even can have all the motifs. The histidine decarboxylase before mutation may further have at least one motif of Motifs (1) to (6) and can have all the motifs.

Motif (1): GDWX$_1$X$_2$X$_3$CNYX$_4$ motif, where X$_1$ represents A, S, or G; X$_2$ represents E, A, or D; X$_3$ represents Y or E, and X$_4$ represents L or R;

Motif (2): EXSNX$_6$X$_7$X$_8$CYLX$_9$ motif, where X$_5$ represents S or G, X$_6$ represents M or L, X$_7$ represents F or Y, X$_8$ represents G or S, and X$_9$ represents G, S, or A;

Motif (3): GSRNGX$_{10}$TPX$_{11}$X$_{12}$MWX$_{13}$AX$_{14}$X$_{15}$S motif, where X$_{10}$ represents H or Q, X$_{11}$ represents L or M, X$_{12}$ represents M or I, X$_{13}$ represents C, E or A, X$_{14}$ represents V or I, and X$_{15}$ represents K or R;

Motif (4): GX$_{16}$X$_{17}$AWX$_{18}$X$_{19}$ motif, where X$_{16}$ represents I or V, X$_{17}$ represents N, D, Q, H, or P, X$_{18}$ represents C, R, or L, and X$_{19}$ represents N, H, or C;

Motif (5): TVX$_{20}$FPCPSX$_{21}$X$_{22}$ motif, where X$_{20}$ represents V or I, X$_{21}$ represents E, V, or A, and X$_{22}$ represents A, D, S, or N; and Motif (6): VWKX$_{23}$X$_{24}$CLAX$_{25}$S motif, where X$_{23}$ represents K or R, X$_{24}$ represents H or Y, and X$_{25}$ represents T or I.

Each motif is determined by analysis of an amino acid sequence designated by SEQ ID NO: 3, as well as histidine decarboxylases derived from other organisms; and these motifs can be determined by comparative analysis of the sequences of histidine decarboxylases derived from each organism described below, the details of which are as follows. The sequence parts of the amino acid sequences corresponding to the respective motifs of the histidine decarboxylase derived from *Photobacterium phosphoreum* (this enzyme is designated "HisDC"), as well as the histidine decarboxylases derived from other organisms (indicated by the UniProt accession Nos.), are described.

Motif (1) corresponds to the amino acid region of GDWAEYCNYL at positions 51 to 60 of the amino acid sequence represented by SEQ ID NO: 3 (Table 1, FIG. 1) and is also herein referred to as GDWX$_1$X$_2$X$_3$CNYX$_4$ motif, where X$_1$ represents [A/S/G], X$_2$ represents [E/A/D], X$_3$ represents [Y/E], and X$_4$ represents [L/R].

TABLE 1

(Motif (1))

| Origin | Uniprot No. | Positions of motif | Homology to SEQ ID NO: 3 (%) |
|---|---|---|---|
| *Serratia rubidaea* | A0A126VDF4 | 51-60 | 84 |
| *Raoultella planticola* (*Klebsiella planticola*) | A0A0H4U8G4 | 51-60 | 84 |
| *Photobacterium damselae* | A0A0H4U975 | 51-60 | 81 |
| *Xenorhabdus poinarii* | A0A068R0F7 | 51-60 | 75 |
| *Klebsiella pneumoniae* | W9B1E6 | 51-60 | 75 |

Motif (2) corresponds to the amino acid region of ESNMFGCYLG at positions 95 to 104 of the amino acid sequence represented by SEQ ID NO: 3 (Table 2, FIG. 2) and is also herein referred to as EXSNX$_6$X$_7$X$_8$CYLX$_9$ motif, where X$_5$ represents [S/G], X$_6$ represents [M/L], X$_7$ represents [F/Y], X$_8$ represents [G/S], and X$_9$ represents [G/S/A].

TABLE 2

(Motif (2))

| Origin | Uniprot No. | Positions of motif | Homology to SEQ ID NO: 3 (%) |
|---|---|---|---|
| *Serratia rubidaea* | A0A126VDF4 | 95-104 | 84 |
| *Raoultella planticola* (*Klebsiella planticola*) | A0A0H4U8G4 | 95-104 | 84 |
| *Photobacterium damselae* | A0A0H4U975 | 95-104 | 81 |
| *Xenorhabdus poinarii* | A0A068R0F7 | 95-104 | 75 |
| *Klebsiella pneumoniae* | W9B1E6 | 95-104 | 75 |
| *Pseudomonas* sp. | A0A0F7XYJ8 | 95-104 | 73 |
| *Chromobacterium* sp. | A0A0J6NJE2 | 95-104 | 70 |
| *Aeromonas salmonicida* | A0A0W0AK78 | 95-104 | 66 |
| *Vibrio nigripulchritudo* | U4DVA0 | 95-104 | 61 |
| *Vibrio neptunius* | A0A0F4P2Z8 | 95-104 | 54 |
| *Vibrio corallilyticus* | A0A1B1VGV7 | 95-104 | 53 |
| *Oligella urethralis* | A0A096BDC0 | 93-102 | 49 |

Motif (3) corresponds to the amino acid region of GSRNGHTPLMMWCAVKS at positions 270 to 286 of the amino acid sequence represented by SEQ ID NO: 3 (Table 3, FIG. 3) and is also herein referred to as GSRNGX$_{10}$TPX$_{11}$X$_{12}$MWX$_{13}$AX$_{14}$X$_{15}$S motif, where X$_{10}$ represents [H/Q], X$_{11}$ represents [L/M], X$_{12}$ represents [M/I], X$_{13}$ represents [C/E/A], X$_{14}$ represents [V/I], and X$_{15}$ represents [K/R].

TABLE 3

(Motif (3))

| Origin | Uniprot No. | Positions of motif | Homology to SEQ ID NO: 3 (%) |
|---|---|---|---|
| *Serratia rubidaea* | A0A126VDF4 | 270-286 | 84 |
| *Raoultella planticola* (*Klebsiella planticola*) | A0A0H4U8G4 | 270-286 | 84 |
| *Photobacterium damselae* | A0A0H4U975 | 270-286 | 81 |
| *Xenorhabdus poinarii* | A0A068R0F7 | 270-286 | 75 |
| *Klebsiella pneumoniae* | W9B1E6 | 270-286 | 75 |

Motif (4) corresponds to the amino acid region of GINAWCNKNSITVVF at positions 314 to 328 of the amino acid sequence represented by SEQ ID NO: 3 (Table 4, FIG. 4) and is also herein referred to as GX$_{16}$X$_{17}$AWX$_{18}$X$_{19}$ motif, where X$_{16}$ represents [UV], X$_{17}$ represents [N/D/Q/H/P], X$_{18}$ represents [C/R/L], and X$_{19}$ represents [N/H/C].

TABLE 4

(Motif (4))

| Origin | Uniprot No. | Positions of motif | Homology to SEQ ID NO: 3 (%) |
|---|---|---|---|
| *Serratia rubidaea* | A0A126VDF4 | 314-328 | 84 |
| *Raoultella planticola* (*Klebsiella planticola*) | A0A0H4U8G4 | 314-328 | 84 |
| *Photobacterium damselae* | A0A0H4U975 | 314-328 | 81 |
| *Xenorhabdus poinarii* | A0A068R0F7 | 314-328 | 75 |
| *Klebsiella pneumoniae* | W9B1E6 | 314-328 | 75 |
| *Pseudomonas* sp. | A0A0F7XYJ8 | 314-328 | 73 |
| *Chromobacterium* sp. | A0A0J6NJE2 | 314-328 | 70 |
| *Aeromonas salmonicida* | A0A0W0AK78 | 314-328 | 66 |
| *Vibrio nigripulchritudo* | U4DVA0 | 314-328 | 61 |

Motif (5) corresponds to the amino acid region of TVVFPCPSEA at positions 325 to 334 of the amino acid sequence represented by SEQ ID NO: 3 (Table 5, FIG. 5) and is also herein referred to as TVX$_{20}$FPCPSX$_{21}$X$_{22}$ motif, where X$_{20}$ represents [V/I], X$_{21}$ represents [E/V/A], and X$_{22}$ represents [A/D/S/N].

TABLE 5

(Motif (5))

| Origin | Uniprot No. | Positions of motif | Homology to SEQ ID NO: 3 (%) |
|---|---|---|---|
| *Serratia rubidaea* | A0A126VDF4 | 325-334 | 84 |
| *Raoultella planticola* (*Klebsiella planticola*) | A0A0H4U8G4 | 325-334 | 84 |
| *Photobacterium damselae* | A0A0H4U975 | 325-334 | 81 |
| *Xenorhabdus poinarii* | A0A068R0F7 | 325-334 | 75 |
| *Klebsiella pneumoniae* | W9B1E6 | 325-334 | 75 |
| *Pseudomonas* sp. | A0A0F7XYJ8 | 325-334 | 73 |

TABLE 5-continued (Motif (5))

| Origin | Uniprot No. | Positions of motif | Homology to SEQ ID NO: 3 (%) |
|---|---|---|---|
| Chromobacterium sp. | A0A0J6NJE2 | 325-334 | 70 |
| Aeromonas salmonicida | A0A0W0AK78 | 325-334 | 66 |
| Vibrio nigripulchritudo | U4DVA0 | 325-334 | 61 |

Motif (6) corresponds to the amino acid region of VWKKHCLATS at positions 335 to 344 of the amino acid sequence represented by SEQ ID NO: 3 (Table 6, FIG. 6) and is also herein referred to as VWKX$_{23}$X$_{24}$CLAX$_{25}$S motif, where X$_{23}$ represents [K/R], X$_{24}$ represents [H/Y], and X$_{25}$ represents [T/I].

TABLE 6

(Motif (6))

| Origin | Uniprot No. | Positions of motif | Homology to SEQ ID NO: 3 (%) |
|---|---|---|---|
| Serratia rubidaea | A0A126VDF4 | 335-344 | 84 |
| Raoultella planticola (Klebsiella planticola) | A0A0H4U8G4 | 335-344 | 84 |
| Photobacterium damselae | A0A0H4U975 | 335-344 | 81 |
| Xenorhabdus poinarii | A0A068R0F7 | 335-344 | 75 |
| Klebsiella pneumoniae | W9B1E6 | 335-344 | 75 |
| Pseudomonas sp. | A0A0F7XYJ8 | 335-344 | 73 |

The mutated histidine decarboxylase can be a histidine decarboxylase in which at least one amino acid residue has been mutated.

The mutated histidine decarboxylase can be more favorable in at least one characteristic thereof than the histidine decarboxylase before mutation. Examples of such a characteristic include histidine decarboxylase activity and histidine decarboxylase stability, such as thermal stability, storage stability, and oxidation resistance. The mutated histidine decarboxylase can be more favorable in either the histidine decarboxylase activity or the histidine decarboxylase stability, and can be more favorable in both of these characteristics as compared to the wild-type. The characteristics may be determined by comparing the wild-type and the mutated histidine decarboxylase in activity at a certain temperature in accordance the methods of evaluation described in the Examples herein. The histidine decarboxylase activity can be confirmed by the relative activity of the enzyme after it is stored at 4° C. as described in the Examples. The relative activities of the mutant enzymes versus the activity of the wild-type enzyme when regarded as 1 can be more than 1, and also can be more than 1.01, 1.03, 1.04, 1.05, 1.1, 1.2, 1.3, 1.4, 1.5, 2.0, 3.0, 4.0, 5.0, 6.0, 7.0, 8.0, 9.0, 10.0, 11.0, or 12.0. Improvement in the histidine decarboxylase thermal stability can be determined by comparing the wild-type and the mutated histidine decarboxylase in residual activity at a high temperature (residual activity after 15 minutes heating at 30° C., 35° C., or 40° C. or more, for example) at a certain concentration. The residual activity can exceed 1.01, 1.03, 1.04, 1.05, 1.1, 1.2, 1.3, 1.4, 1.5, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, or 20.0-fold as compared with the residual activity of the wild-type.

Examples of mutation of the amino acid of the mutated histidine decarboxylase include deletion, substitution with another amino acid residue, and addition and insertion of at least one amino acid residue; substitution with another amino acid residue is a particular example. The mutation of the amino acid residue may be introduced into one region in the amino acid sequence or introduced into a plurality of different regions. The number of mutations in the mutated histidine decarboxylase may be at least one, and can be 1 to 100, 1 to 80, 1 to 50, 1 to 30, 1 to 20, 1 to 10, or 1 to 5.

When the wild-type histidine decarboxylase includes at least one of Motifs (1) to (6), at least one amino acid residue in these motifs can be mutated. That is to say, the mutated histidine decarboxylase can have one or more mutation(s) of one amino acid residue or a combination of mutations of two or more amino acid residues in Motif (1), mutation of one amino acid residue or a combination of mutations of two or more amino acid residues in Motif (2), mutation of one amino acid residue or a combination of mutations of two or more amino acid residues in Motif (3), mutation of one amino acid residue or a combination of mutations of two or more amino acid residues in Motif (4), mutation of one amino acid residue or a combination of mutations of two or more amino acid residues in Motif (5), and mutation of one amino acid residue or a combination of mutations of two or more amino acid residues in Motif (6).

Examples of the mutation of at least one amino acid residue in Motif (1) include mutation of at least one amino acid residue in the CNY motif (corresponding to position 57 to position 59 of SEQ ID NO: 3) and mutation of $X_2$ (corresponding to position 55 of SEQ ID NO: 3) in Motif (1). The at least one amino acid residue in the CNY motif can be C. The mutation of C can be a substitution with an amino acid residue other than C, such as with A, S, T, R, or G. The mutation of $X_2$ can be a substitution with an amino acid residue other than $X_2$, and C is a particular example.

Examples of the mutation of at least one amino acid residue in Motif (2) include mutation of at least one amino acid residue in the CYL motif (corresponding to position 101 to position 103 of SEQ ID NO: 3), mutation of $X_5$ (corresponding to position 96 of SEQ ID NO: 3), and mutation of $X_6$ (corresponding to position 98 of SEQ ID NO: 3) in Motif (2). The at least one amino acid residue in the CYL motif can includes C or Y, and C is a particular example. The mutation of C can be a substitution with an amino acid residue other than C, such as with A, S, or V. The mutation of Y can be a substitution with an amino acid residue other than Y, such as with F. The mutation of $X_5$ can be a substitution with an amino acid residue other than $X_5$, such as S. The mutation of $X_6$ can be a substitution with an amino acid residue other than $X_6$, such as with A, S, or V.

Examples of the mutation of at least one amino acid residue in Motif (3) include mutation of $X_{12}$ (corresponding to position 279 of SEQ ID NO: 3), mutation of M (corresponding to position 280 of SEQ ID NO: 3), and mutation of $X_{13}$ (corresponding to position 282 of SEQ ID NO: 3) in Motif (3). The mutation of $X_{12}$ can be a substitution with an amino acid residue other than $X_{12}$, such as with I. The mutation of M can be a substitution with an amino acid residue other than M, such as with L or I. The mutation of $X_{13}$ can be a substitution to an amino acid residue other than $X_{13}$, such as with A, S, or V.

Examples of the mutation of at least one amino acid residue in Motif (4) include mutation of $X_{18}$ (corresponding to position 319 of SEQ ID NO: 3) in Motif (4). The mutation of $X_{18}$ can be a substitution with an amino acid residue other than $X_{18}$, such as with A, S, or V.

Examples of the mutation of at least one amino acid residue in Motif (5) include mutation of $X_{20}$ (corresponding to position 327 of SEQ ID NO: 3) in Motif (5) and mutation in the FPCPS motif (corresponding to position 328 to position 332 of SEQ ID NO: 3). The mutation in the FPCPS motif can be a mutation of C (corresponding to position 330 of SEQ ID NO: 3). The mutation of $X_{20}$ can be a substitution with an amino acid residue other than $X_{20}$, such as with I. The mutation of C can be a substitution to an amino acid residue other than C, such as with A, S, or V.

Examples of the mutation of at least one amino acid residue in Motif (6) include mutation in the CLATS motif (corresponding to position 340 to position 344 of SEQ ID NO: 3) in Motif (6). The mutation in the CLATS motif can be a mutation of C (corresponding to position 340 of SEQ ID NO: 3). The mutation of C can be a substitution to an amino acid residue other than C, such as with A.

Examples of the mutation of at least one amino acid residue in the mutated histidine decarboxylase include not only the mutation sites exemplified above but also the mutations described below, and can include at least one of the following:

mutation of tryptophan corresponding to position 15 of SEQ ID NO: 3, such as substitution with phenylalanine;

mutation of asparagine corresponding to position 21 of SEQ ID NO: 3, such as substitution with histidine;

mutation of glutamine corresponding to position 22 of SEQ ID NO: 3, such as substitution with arginine;

mutation of methionine corresponding to position 43 of SEQ ID NO: 3, such as substitution with leucine;

mutation of glutamic acid corresponding to position 55 of SEQ ID NO: 3, such as substitution with serine;

mutation of cysteine corresponding to position 57 of SEQ ID NO: 3, such as substitution with alanine, glycine, arginine, serine, or threonine;

mutation of serine corresponding to position 96 of SEQ ID NO: 3, such as substitution with glycine;

mutation of methionine corresponding to position 98 of SEQ ID NO: 3, such as substitution with valine;

mutation of cysteine corresponding to position 101 of SEQ ID NO: 3, such as substitution with alanine, serine, or valine;

mutation of tyrosine corresponding to position 102 of SEQ ID NO: 3, such as substitution with phenylalanine;

mutation of tyrosine corresponding to position 114 of SEQ ID NO: 3, such as substitution with phenylalanine;

mutation of leucine corresponding to position 130 of SEQ ID NO: 3, such as substitution with isoleucine;

mutation of isoleucine corresponding to position 132 of SEQ ID NO: 3, such as substitution with leucine or methionine;

mutation of tyrosine corresponding to position 147 of SEQ ID NO: 3, such as substitution with phenylalanine;

mutation of methionine corresponding to position 185 of SEQ ID NO: 3, such as substitution with threonine, leucine, isoleucine, serine, or alanine;

mutation of tyrosine corresponding to position 196 of SEQ ID NO: 3, such as substitution with phenylalanine;

mutation of methionine corresponding to position 234 of SEQ ID NO: 3, such as substitution with alanine;

mutation of methionine corresponding to position 279 of SEQ ID NO: 3, such as substitution with isoleucine;

mutation of methionine corresponding to position 280 of SEQ ID NO: 3, such as substitution with leucine or isoleucine;

mutation of cysteine corresponding to position 282 of SEQ ID NO: 3, such as substitution with alanine, serine, or valine;

mutation of cysteine corresponding to position 319 of SEQ ID NO: 3, such as substitution with alanine, serine, or valine;

mutation of valine corresponding to position 327 of SEQ ID NO: 3, such as substitution to isoleucine;

mutation of cysteine corresponding to position 330 of SEQ ID NO: 3, such as substitution with alanine, serine, or valine;

mutation of cysteine corresponding to position 340 of SEQ ID NO: 3, such as substitution to alanine; and mutation of methionine corresponding to position 377 of SEQ ID NO: 3, such as substitution with threonine, leucine, isoleucine, or alanine.

The mutated histidine decarboxylase can also have at least two amino acid residues therein mutated.

When the wild-type histidine decarboxylase includes at least one motif of Motifs (1) to (6), at least two amino acid residues in these motifs may be mutated. Namely, the mutated histidine decarboxylase may have at least two mutations of the amino acid residues such as mutation of one amino acid residue or a combination of two or more mutations of amino acid residues in Motif (1), mutation of one amino acid residue or a combination of two or more mutations of amino acid residues in Motif (2), mutation of one amino acid residue or a combination of two or more mutations of amino acid residues in Motif (3), mutation of one amino acid residue or a combination of two or more mutations of amino acid residues in Motif (4), mutation of one amino acid residue or a combination of two or more mutations of amino acid residues in Motif (5), and mutation of one amino acid residue or a combination of two or more mutations of amino acid residues in Motif (6).

When the mutated histidine decarboxylase has a combination of two or more mutations of amino acid residues, this combination of two or more mutations can be:

a combination of a mutation of at least one amino acid residue in Motif (1) and a mutation of at least one amino acid residue in at least one of Motifs (2) to (6), a combination of a mutation of at least one cysteine in Motif (1) and a mutation of at least one cysteine in at least one of Motifs (2) to (6), a combination of a substitution of at least one cysteine in Motif (1) to serine and a substitution of at least one cysteine in at least one of Motifs (2) to (6) with alanine, serine, or valine, and/or a combination of (i) a substitution of cysteine in the CNY motif of Motif (1) with serine, and (ii) a substitution of at least one of cysteine in the CYL motif of Motif (2), cysteine that is $X_{12}$ of Motif (3), cysteine that is $X_{18}$ of Motif (4), cysteine that is $X_{20}$ of Motif (5), and cysteine in the CLATS motif of Motif (6), with alanine, serine, or valine.

When the mutated histidine decarboxylase has a combination of three or more mutations, the combination of three or more mutations can be:

a combination of a mutation of at least one amino acid residue in Motif (1), a mutation of at least one amino acid residue in Motif (2), and a mutation of at least one amino acid residue in at least one of Motifs (3) to (6), a combination of a mutation of at least one cysteine in Motif (1), a mutation of at least one cysteine in Motif (2), and a mutation of at least one cysteine in at least one of Motifs (3) to (6), a combination of a substitution of at least one cysteine in Motif (1) with serine, a substitution of at least one cysteine in Motif (2) with valine, and a substitution of at least one cysteine in at least one motif of Motifs (3) to (6) with alanine, serine, or valine, and/or a combination of
(i) a substitution of cysteine in the CNY motif of Motif (1) with serine,
(ii) a substitution of cysteine in the CYL motif of Motif (2) with valine, and
(iii) a substitution of at least one of cysteine that is $X_{12}$ in Motif (3), cysteine that is $X_{18}$ in Motif (4), cysteine that is $X_{20}$ in Motif (5), and cysteine in the CLATS motif of Motif (6), with alanine, serine, or valine.

The histidine decarboxylase before mutation, that is, the wild-type histidine decarboxylase, may have any of the following amino acid sequences (a) to (c):
(a) the amino acid sequence represented by SEQ ID NO: 3;
(b) an amino acid sequence including one or several amino acid residue substitutions, deletions, insertions, or additions in the amino acid sequence represented by SEQ ID NO: 3; or
(c) an amino acid sequence having 90% or more identity to the amino acid sequence represented by SEQ ID NO: 3.

The amino acid sequence represented by SEQ ID NO: 3 is a *Photobacterium phosphoreum*-derived histidine decarboxylase and is encoded by a base sequence represented by SEQ ID NO: 1, that is, a full-length base sequence of a *Photobacterium phosphoreum*-derived histidine decarboxylase gene.

The amino acid residue that can be a target of mutation such as substitution, deletion, insertion, or addition can be normally L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), or glycine (G), which are natural L-α-amino acids. When the mutation is substitution, addition, or insertion, the amino acid residue to be substituted, added, or inserted is the same as the amino acid residue to be mutated described above. In the following, L and a may be omitted in the amino acid notation.

The amino acid sequence of (b) may include mutation (e.g., substitution, deletion, insertion, and addition) of one or several amino acid residues. The number of the mutation(s) can be 1 to 50, for example, 1 to 40, 1 to 30, 1 to 20, or 1 to 10 (e.g., 1, 2, 3, 4, or 5).

The amino acid sequence of (c) may have at least 90% or more amino acid sequence identity to the amino acid sequence represented by SEQ ID NO: 3. The identity percentage of the amino acid sequence may be 92% or more, 95% or more, even 97% or more, 98% or more, or 99% or more.

Proteins determined by the amino acid sequences of (b) and (c) have an activity of 50% or more, 60% or more, 70% or more, 80% or more, 90% or more, or 95% or more of the histidine decarboxylase activity of a protein having the amino acid sequence of (a) when measured under the same condition.

The amino acid sequence identity can be determined using the algorithm BLAST by Karlin and Altschul (Pro. Natl. Acad. Sci. USA, 90, 5873 (1993)) or FASTA by Pearson (Methods Enzymol., 183, 63 (1990)), for example. Programs called BLASTP have been developed based on this algorithm BLAST (refer to ncbi.nlm.nih.gov), and the amino acid sequence identity may be calculated using these programs by default settings. For the amino acid sequence identity, a numerical value when, using the software GENETYX Ver. 7.0.9 by Genetyx Corporation employing the Lipman-Pearson method and using the full length of a polypeptide part encoded by ORF, Similarity is calculated in terms of percentage with a setting of Unit Size to Compare=2 may be used, for example. For the amino acid sequence identity, the smallest value among the values derived from these calculations may be employed.

The position of the amino acid residue to be mutated in the amino acid sequence represented by SEQ ID NO: 3 for preparation of (b) the amino acid sequence including one or several amino acid residue substitutions, deletions, insertions, or additions in the amino acid sequence of SEQ ID NO: 3 and (c) the amino acid sequence having 90% or more identity to the amino acid sequence represented by SEQ ID NO: 3 is obvious to the skilled person; the mutation can be introduced using amino acid sequences alignment for reference, for example. Specifically, the skilled person can 1) compare a plurality of homologue amino acid sequences (e.g., the amino acid sequence represented by SEQ ID NO: 3 and another homologue amino acid sequence) with each other, 2) reveal a relatively conserved region and a relatively not conserved region, and then 3) predict a region that can play an important role for function and a region that cannot play an important role for function from each of the relatively conserved region and the relatively not conserved region, and can thus recognize structure-function correlation. Consequently, the skilled person can determine the amino acid sequences of (b) and (c) in which mutation of one or more amino acid residues improving thermal stability is introduced.

When mutation of an amino acid residue is introduced to the amino acid sequence represented by SEQ ID NO: 3 for preparation of:
(b) the amino acid sequence including one or several amino acid residue substitutions, deletions, insertions, or additions in the amino acid sequence of SEQ ID NO: 3 and/or
(c) the amino acid sequence having 90% or more identity to the amino acid sequence represented by SEQ ID NO: 3, and when the mutation of the amino acid residue is substitution, such substitution of the amino acid residue may be conservative substitution. The term "conservative substitution" can refer to substituting a certain amino acid residue with an amino acid residue having a similar side chain. Families of the amino acid residue having a similar side chain are well known in the field. Examples of such families include amino acids having a basic side chain (e.g., lysine, arginine, and histidine), amino acids having an acidic side chain (e.g., aspartic acid and glutamic acid), amino acids having an uncharged polar side chain (e.g., asparagine, glutamine, serine, threonine, tyrosine, and cysteine), amino acids having a nonpolar side chain (e.g., glycine, alanine, valine, leucine, isoleucine, proline, phenylalanine, methionine, and tryptophan), amino acids having a β-position-branched side chain (e.g., threonine, valine, and isoleucine), amino acids having an aromatic side chain (e.g., tyrosine, phenylalanine, tryptophan, and histidine), amino acids having a hydroxy group (e.g., alcoholic and phenolic)-containing side chain (e.g., serine, threonine, and tyrosine), and amino acids having a sulfur-containing side chain (e.g., cysteine and methionine). The amino acids having an uncharged polar side chain and the amino acids having a nonpolar side chain may be collectively called neutral amino acids. The conservative substitution of the amino acid may be substitution between aspartic acid and glutamic acid, substitution among arginine, lysine, and histidine, substitution between tryptophan and phenylalanine, substitution between phenylalanine and valine, substitution among leucine, isoleucine, and alanine, and substitution between glycine and alanine.

The amino acid sequence represented by SEQ ID NO: 3 includes Motifs (1) to (6) shown in the first example. The amino acid sequences of (b) and (c) also can conserve at least one of Motifs (1) to (6), can conserve at least one of Motifs (1), (2), (5), and (6), and can conserve all of Motifs (1), (2), (5), and (6).

When the mutated histidine decarboxylase has any one of above (a) to (c), examples of the mutation can include the following mutations including the mutation sites illustrated in Motifs (1) to (6) described above; and the mutated histidine decarboxylase can have at least one of the following mutations:

mutation of tryptophan at position 15, such as substitution with phenylalanine;

mutation of asparagine at position 21, such as substitution with histidine;

mutation of glutamine at position 22, such as substitution to arginine;

mutation of methionine at position 43, such as substitution with leucine;

mutation of glutamic acid at position 55, such as substitution with serine;

mutation of cysteine at position 57, such as substitution with alanine, glycine, arginine, serine, or threonine;

mutation of serine at position 96, such as substitution with glycine;

mutation of methionine at position 98, such as substitution with valine;

mutation of cysteine at position 101, such as substitution with alanine, serine, or valine;

mutation of tyrosine at position 102, such as substitution with phenylalanine;

mutation of tyrosine at position 114, such as substitution with phenylalanine;

mutation of leucine at position 130, such as substitution with isoleucine;

mutation of isoleucine at position 132, such as substitution with leucine, or methionine;

mutation of tyrosine at position 147, such as substitution with phenylalanine;

mutation of methionine at position 185, such as substitution with threonine, leucine, isoleucine, serine, or alanine;

mutation of tyrosine at position 196, such as substitution with phenylalanine;

mutation of methionine at position 234, such as substitution with alanine;

mutation of methionine at position 279, such as substitution with isoleucine;

mutation of methionine at position 280, such as substitution with leucine or isoleucine;

mutation of valine at position 327, such as substitution with isoleucine; and mutation of methionine at position 377, such as substitution with threonine, leucine, isoleucine, or alanine).

Furthermore, even when any of Motifs (1) to (6) is not conserved, the mutated histidine decarboxylase may have at least one of the following mutations:

mutation of asparagine at position 21, such as substitution with histidine;

mutation of glutamine at position 22, such as substitution with arginine;

mutation of methionine at position 43, such as substitution with leucine;

mutation of glutamine at position 55, such as substitution with serine;

mutation of cysteine at position 57, such as substitution with alanine, serine, threonine, arginine, or glycine;

mutation of serine at position 96, such as substitution with glycine;

mutation of methionine at position 98, such as substitution with valine;

mutation of cysteine at position 101, such as substitution with alanine, serine, or valine;

mutation of leucine at position 130, such as substitution with isoleucine;

mutation of isoleucine at position 132, such as substitution with leucine, or methionine;

mutation of methionine at position 185, such as substitution with threonine, leucine, isoleucine, serine, or alanine;

mutation of methionine at position 234, such as substitution with alanine;

mutation of methionine at position 279, such as substitution with isoleucine;

mutation of methionine at position 280, such as substitution with leucine or isoleucine;

mutation of cysteine at position 282, such as substitution with alanine, serine, or valine;

mutation of cysteine at position 319, such as substitution with alanine, serine, or valine;

mutation of valine at position 327, such as substitution with isoleucine;

mutation of cysteine at position 330, such as substitution with alanine, serine, or valine;

mutation of cysteine at position 340, such as substitution with alanine; and mutation of methionine at position 377, such as substitution with threonine, leucine, isoleucine or alanine.

An amino acid residue after mutation may be substituted with an amino acid residue having a similar side chain. Examples of the amino acid residue having a similar side chain include amino acids having a basic side chain (e.g., lysine, arginine, and histidine), amino acids having an acidic side chain (e.g., aspartic acid and glutamic acid), amino acids having an uncharged polar side chain (e.g., asparagine, glutamine, serine, threonine, tyrosine, and cysteine), amino acids having a nonpolar side chain (e.g., glycine, alanine, valine, leucine, isoleucine, proline, phenylalanine, methionine, and tryptophan), amino acids having a β-position-branched side chain (e.g., threonine, valine, and isoleucine), amino acid having an aromatic side chain (e.g., tyrosine, phenylalanine, tryptophan, and histidine), amino acids having a hydroxy group-containing side chain (e.g., alcohol and a phenoxy group-containing side chain) (e.g., serine, threonine, and tyrosine), and amino acids having a sulfur-containing side chain (e.g., cysteine and methionine).

The mutated histidine decarboxylase may have another peptide component, such as a tag moiety, at its C-terminus or N-terminus. Examples of the other peptide component include a peptide component that facilitates purification of a target protein, such as tag moieties such as a histidine tag and Strep-tag II; proteins generally used for the purification of a target protein such as glutathione-S-transferase and a maltose binding protein; a peptide component that improves the solubility of a target protein (e.g., Nus-tag); a peptide component functioning as a chaperon (e.g., Trigger Factor); and a peptide component as a linker that links with a protein or protein domain having another function or both. The mutated histidine decarboxylase may have an initiation methionine residue at its N-terminus.

The mutated histidine decarboxylase may have additional mutation, such as substitution, deletion, insertion, and addition, of one or several amino acid residues in addition to the above mutation so long as the characteristics described above are maintained. The number of the additional mutation is 1 to 100, for example, 1 to 50, 1 to 40, 1 to 30, 1 to 20 or 1 to 10 (e.g., 1, 2, 3, 4, or 5). The skilled person can produce such a mutated oxidase maintaining the characteristics described above as appropriate.

Consequently, the mutated histidine decarboxylase may be any of the following:
i. A mutated histidine decarboxylase including an amino acid sequence in which at least one amino acid residue in Motifs (1) to (6) is mutated (e.g., substituted) in an amino acid sequence of a histidine decarboxylase before mutation (wild-type) having at least one motif selected from the group consisting of Motifs (1) to (6), and wherein the mutated histidine decarboxylase has higher histidine decarboxylase activity and/or stability (e.g., thermal stability, storage stability, and oxidation resistance) than the wild-type histidine decarboxylase, (ii) A mutated histidine decarboxylase having an amino acid sequence having mutation (e.g., substitution) in which at least one amino acid residue in an amino acid sequence of a histidine decarboxylase having (a) the amino acid sequence represented by SEQ ID NO: 3, (b) the amino acid sequence including one or several amino acid residue substitutions, deletions, insertions, or additions in the amino acid sequence represented by SEQ ID NO: 3, or (c) the amino acid sequence having 90% or more identity to the amino acid sequence represented by SEQ ID NO: 3 is mutated (e.g., substituted) and having higher histidine decarboxylase activity and/or stability (e.g., thermal stability, storage stability, and oxidation resistance) than the wild-type histidine decarboxylase.

The mutated histidine decarboxylase has the mutation described above and may thereby include an amino acid sequence having at least 90% or more amino acid sequence identity to the amino acid residue of the histidine decarboxylase before mutation (wild-type). The identity percentage of the amino acid sequence may be 92% or more, 95% or more, 97% or more, 98% or more or 99% or more. The definition and examples of the amino acid sequence identity are as described above.

When the mutation of the amino acid residue is substitution, such substitution of the amino acid residue may be conservative substitution. The definition and examples of the term "conservative substitution" are as described above.

The mutated histidine decarboxylase can be prepared using a transformant expressing the mutated histidine decarboxylase or using a cell-free system or the like. The transformant expressing the mutated histidine decarboxylase can be produced by producing an expression vector including a polynucleotide encoding the mutated histidine decarboxylase and then introducing this expression vector into a host, for example. The polynucleotide encoding the mutated histidine decarboxylase may be DNA or RNA, and DNA is a particular example.

The expression vector may include the polynucleotide encoding the mutated histidine decarboxylase; examples thereof include cell system vectors expressing a protein in a host and cell-free system vectors using a protein translation system. The expression vector may also be a plasmid, a virus vector, a phage, an integrative vector, or an artificial chromosome. The integrative vector may be of the type that the entire vector is integrated into the genome of a host cell. Alternatively, the integrative vector may be a vector of the type that only part of the vector, such as an expression unit including a polynucleotide of the present invention encoding the mutated histidine decarboxylase of the present invention and a promoter operably coupled thereto, is integrated into the genome of a host cell. The expression vector may further be a DNA vector or an RNA vector.

The expression vector may further include regions such as regions encoding a promoter, a terminator, and a drug (e.g., tetracycline, ampicillin, kanamycin, hygromycin, and phosphinothricin) resistance gene in addition to the polynucleotide encoding the mutated histidine decarboxylase. The expression vector may be a plasmid or an integrative vector. The expression vector may be a virus vector or a vector for a cell-free system. The expression vector may include a polynucleotide encoding another peptide component that can be added to the mutated histidine decarboxylase on the 3'- or 5'-terminal side relative to the polynucleotide encoding the mutated histidine decarboxylase. Examples of the polynucleotide encoding the other peptide component include a polynucleotide encoding the peptide component that facilitates purification of a target protein described above, a polynucleotide encoding the peptide component that improves the solubility of a target protein described above, a polynucleotide encoding a peptide component functioning as a chaperon, and a polynucleotide encoding a peptide component as a linker that links with a protein or protein domain having another function or both. Various expression vectors including the polynucleotide encoding the other peptide component can be used. Consequently, such expression vectors may be used in order to produce the expression vector including the polynucleotide encoding the mutated histidine decarboxylase; examples of the expression vectors include an expression vector including a polynucleotide encoding a peptide component that facilitates purification of a target protein (e.g., pET-15b, pET-51b, pET-41a, and pMAL-p5G), an expression vector including a polynucleotide encoding a peptide component that improves the solubility of a target protein (e.g., pET-50b), an expression vector including a polynucleotide encoding a peptide component functioning as a chaperon (e.g., pCold TF), and an expression vector including a polynucleotide coding a peptide component as a linker that links with a protein or protein domain having another function or both. The expression vector may include a region encoding a cleavage site by protease between the polynucleotide encoding the mutated histidine decarboxylase and the polynucleotide encoding the other peptide component. With this structure, cleavage between the mutated histidine decarboxylase and the other peptide component added thereto is enabled after protein expression.

Examples of the host for expressing the mutated histidine decarboxylase include various prokaryotic cells including

*Escherichia* bacteria such as *Escherichia coli, Corynebacterium* bacteria (e.g., *Corynebacterium glutamicum*), and *Bacillus* bacteria (e.g., *Bacillus subtilis*); and various eukaryotic cells including *Saccharomyces* bacteria (e.g., *Saccharomyces cerevisiae*), *Pichia* bacteria (e.g., *Pichia stipitis*), and *Aspergillus* bacteria (e.g., *Aspergillus oryzae*). For the host, a strain depleted of a certain gene may be used. Examples of the transformant include a transformant having an expression vector in cytoplasm and a transformant in which a target gene is introduced to a genome.

The transformant expressing the mutated histidine decarboxylase can be cultured in a culture medium having a composition described below, for example, using a certain culture apparatus (e.g., a test tube, a flask, and a jar fermenter). Culture conditions can be set as appropriate. Specifically, the culture temperature may be 10° C. to 37° C., pH may be 6.5 to 7.5, and the culture time may be 1 hour to 100 hours. Culture may be performed while a dissolved oxygen concentration is controlled. In this case, a dissolved oxygen concentration (a DO value) in a culture liquid may be used as an indicator of control. Ventilation and stirring conditions can be controlled such that a relative dissolved oxygen concentration DO value with the oxygen concentration of the atmosphere as 21% does not fall below 1 o 10%, for example, and or 3% to 8%. Culture may be batch culture or fed-batch culture. In the case of fed-batch culture, a solution as a sugar source or a solution containing phosphoric acid is added to the culture liquid in succession continuously or discontinuously, whereby culture can be continued.

The host to be transformed is as described above; the *Escherichia coli* strain can be *Escherichia coli* JM 109 strain, DH5a strain, HB101 strain, BL21 (DE3) strain, and the like as subspecies of *Escherichia coli* K12 strain. A method for performing transformation and a method for selecting a transformant are described in Molecular Cloning: A Laboratory Manual, 3rd edition, Cold Spring Harbor press (2001/01/15), etc. The following describes a method for producing transformed *Escherichia coli* and producing a certain oxidase using the same as an example more specifically.

For a promoter expressing the polynucleotide encoding the mutated histidine decarboxylase, promoters that are normally used for heteroprotein production in *E. coli* can be used; examples thereof include strong promoters such as PhoA, PhoC, a T7 promoter, a lac promoter, a trp promoter, a trc promoter, a tac promoter, a PR promoter and a PL promoter of λ phage, and a T5 promoter, and PhoA, PhoC, and lac are particular examples. Examples of a vector include pUC (e.g., pUC19 and pUC18), pSTV, pBR (e.g., pBR322), pHSG (e.g., pHSG299, pHSG298, pHSG399, pHSG398), RSF (e.g., RSF1010), pACYC (e.g., pACYC177 and pACYC184), pMW (e.g., pMW119, pMW118, pMW219, and pMW218), pQE (e.g., pQE30), and derivatives thereof. A vector of phage DNA may be used as another vector. Further, an expression vector that includes a promoter and can express an insertion DNA sequence may be used. The vector may be pUC, pSTV, or pMW.

A terminator as a transcription termination sequence may be coupled to the downstream of the polynucleotide encoding the mutated histidine decarboxylase. Examples of such a terminator include a T7 terminator, an fd phage terminator, a T4 terminator, a terminator of a tetracycline resistance gene, and a terminator of *Escherichia coli* trpA gene.

A vector for introducing the polynucleotide encoding the mutated histidine decarboxylase into *Escherichia coli* can be what is called a multicopy type vector; examples thereof include plasmids having a ColE1-derived replication origin such as pUC type plasmids and pBR322 type plasmids and derivatives thereof. The "derivatives" mean products with plasmids modified by substitution, depletion, insertion, and/or addition and the like of bases.

The vector can have a marker such as an ampicillin resistance gene in order to select a transformant. Expression vectors having a strong promoter are commercially available as a plasmid.

*Escherichia coli* is transformed using the obtained expression vector, and this *Escherichia coli* is cultured, whereby the mutated histidine decarboxylase can be obtained.

For a culture medium, culture media normally used for culturing *Escherichia coli* such as an M9-casamino acid culture medium and LB culture medium may be used. The culture medium may contain a certain carbon source, nitrogen source, and coenzyme (e.g., pyridoxine hydrochloride). Specifically, peptone, yeast extract, NaCl, glucose, $MgSO_4$, ammonium sulfate, potassium dihydrogenphosphate, ferric sulfate, manganese sulfate, and the like may be used. Culture conditions and production-inducing conditions are selected as appropriate in accordance with the types of the marker of the vector, the promoter, and the chosen host bacteria.

The mutated histidine decarboxylase is collected by the following method. After the transformant is collected, the mutated histidine decarboxylase can be obtained crushing (e.g., sonication and homogenization) or dissolving (e.g., lysozyme treatment) the bacterial cells. After the crushing or dissolving, the products are subjected to techniques such as extraction, precipitation, filtration, and column chromatography, whereby the mutated histidine decarboxylase can be obtained. Alternatively, the mutated histidine decarboxylase may be recovered after the transformant is subjected to the heat treatment as mentioned above.

The mutated histidine decarboxylase can be used for analysis of histidine.

The sample is not limited to a particular sample so long as it is a sample suspected to contain histidine; examples thereof include living body-derived samples, such as blood, urine, saliva, and tears, and foods and drinks, such as nutritional drinks and amino acid drinks. Histidine in the sample may be low in concentration (e.g., a concentration of less than 1 mM such as 1 µM or more and less than 1 mM) or high in concentration (e.g., a concentration of 1 mM or more such as 1 mM or more and less than 1 M).

When the specimen is derived from a living body, although the subject from which the specimen is collected is not particularly restricted, the subject can be one who wishes to confirm whether the subject is suffering from a disease such as Crohn's disease, inflammatory bowel diseases such as ulcerative colitis, histidinemia, cardiac cachexia, or cancer; these being the diseases in which histidine can act as a biomarker. By so doing, whether the subject is suffering from these diseases, i.e., the suffering risk thereof, can be analyzed precisely, quickly, conveniently, and cheaply. When the disease is ulcerative colitis, the subject can be one who is in a remission phase of ulcerative colitis. With this, the recurrence risk of ulcerative colitis can be evaluated.

In the measurement of histidine, the mutated histidine decarboxylase and the 4-imidazolyl acetaldehyde generating enzyme can be used concurrently. By so doing, the histidine in the specimen can be readily analyzed. The detection object in the case when the 4-imidazolyl acetaldehyde generating enzyme is concurrently used is not particularly restricted so far as histidine in the specimen can be measured, and it can be any of 4-imidazolyl acetaldehyde, a reduced type electron donor, as well as byproducts such as ammonia and hydrogen peroxide produced. Alternatively, this may be conjugated with other reaction so as to detect a product of the conjugate reaction.

When the 4-imidazolyl acetaldehyde generating enzyme is a histamine dehydrogenase, illustrative examples of the reaction and the conjugate reaction for measurement of histidine include the following reactions:

Reaction Catalyzed by the Histidine Decarboxylase:

histidine→histamine+$CO_2$

Reaction Catalyzed by the Histamine Dehydrogenase:

histamine+oxidized type electron donor→4-imidazolyl acetaldehyde+$NH_2$+reduced type electron donor 1-$PMSH_2$ Conjugate Reaction:

reduced type electron donor+tetrazolium salt (WST-8)→oxidized type electron donor+WST-8 (red color)

Examples of the electron donor include 1-methoxy phenazine methosulfate (1-methoxy PMS (oxidized type)/1-$PMSH_2$ (reduced type)).

When the conjugate reaction is used, measurement of histidine may be made by using, in addition to the histidine decarboxylase and the histamine dehydrogenase, the electron donor and the tetrazolium salt. Specifically, the specimen and the histidine decarboxylase are subjected to the enzymatic reaction in an aqueous solution (for example, in a buffer solution); and then, the electron donor, the tetrazolium salt, and the histamine dehydrogenase are mixed therein so as to cause the enzymatic reaction; and finally, absorbance (about 470 nm) of WST-8 (red color) thus produced is detected to measure histidine. The measurement may be made qualitatively or quantitatively. The measurement may be done, for example, either on the basis of an end-point method in which the measurement is done until all the substrates react, or on the basis of a rate method (initial rate method).

When the 4-imidazolyl acetaldehyde generating enzyme is a histamine oxidase, illustrative examples of the reaction and the conjugate reaction for measurement of histidine include the following reactions:

Reaction catalyzed by the histidine decarboxylase:

histidine→histamine+$CO_2$

Reaction catalyzed by the histamine oxidase:

histamine+$H_2O$+$O_2$→4-imidazolyl acetaldehyde+$NH_3$+$H_2O_2$

Conjugate reaction (reaction catalyzed by peroxidase):

$2H_2O_2$+4-aminoantipyrine+phenol→quinonimine dye+$4H_2O$

When the coupled reaction is used, measurement of histidine can be performed using 4-aminoantipyrine, phenol, and peroxidase in addition to the histidine decarboxylase and the histamine oxidase. Specifically, in an aqueous solution (e.g., a buffer solution), the sample is subjected to the enzymatic reaction with the histidine decarboxylase, then the mixed sample obtained by mixing it with 4-aminoantipyrine, phenol, and peroxidase is subjected to the enzymatic reaction, and finally the absorbance (ca. 500 nm) of the produced quinoneimine dye is detected, whereby histidine is measured. The measurement can be performed qualitatively or quantitatively. The measurement may be performed based on the endpoint assay, which performs measurement until all substrates react, or performed based on the rate assay (the initial velocity assay), for example. The amount of oxygen required for the oxidation reaction is very small, and a required amount of oxygen can be covered by dissolved oxygen in the reaction system, and thus there is normally no need to compulsorily supply oxygen or gas containing oxygen to the reaction system.

The histamine oxidase can be used for a hydrogen peroxide electrode. The amount of histamine in the sample can be specifically evaluated by using such a hydrogen peroxide electrode.

The histidine decarboxylase may be included, together with the 4-imidazolyl acetaldehyde generating enzyme, into a histamine measurement kit. The histamine measurement kit may further include other reagents such as, for example, at least one reagent selected from the group consisting of a buffer solution or a buffering salt for reactions, a hydrogen peroxide detecting reagent, an ammonia detecting reagent, and a 4-imidazolyl acetaldehyde detecting reagent.

The buffer solution or buffer salt for reaction can be used in order to maintain pH in a reaction liquid at a value suitable for a target oxidase reaction.

When the 4-imidazolyl acetaldehyde generating enzyme is a histamine dehydrogenase, the hydrogen peroxide detection reagent can be used when hydrogen peroxide is detected through color development, fluorescence, or the like, for example. Examples of such a reagent include a combination of peroxidase and a coloring agent that can be a substrate thereof; specific examples thereof include, but are not limited to, a combination of horseradish peroxidase, 4-aminoantipyrine, and phenol.

Examples of the ammonia detection reagent include the indophenol method combining phenol and hypochlorous acid.

Examples of the 4-imidazolyl acetaldehyde detecting reagent include electron donors such as 1-methoxy PMS.

The histidine decarboxylase may be used as a composing element of a histidine detecting system. The histidine detecting system is required to be a detecting system with which histidine can be measured, analyzed, and the like. Illustrative examples thereof include a detecting system for histidine analysis/measurement and an enzyme sensor for histidine analysis/measurement.

The histidine decarboxylase can be a component of a detection system for histidine analysis/measurement together with the 4-imidazolyl acetaldehyde generating enzyme and a device. Each enzyme may be present as a unit independent of a micro device that can be supplied to the device in use or may be injected into, fixed to, or placed at the device in advance. Each enzyme can be provided in the form of being injected into, fixed to, or placed at the device in advance. Each enzyme is fixed to or placed at the device directly or indirectly. For the device, a micro device such as a microchannel chip including a channel can be suitably used, for example.

The detection system for histidine analysis/measurement may include other components. Examples of the other components include a buffer solution or buffer salt for reaction, a hydrogen peroxide detection reagent, an ammonia detection reagent, and a 4-imidazolyl acetaldehyde detection reagent. In the detection system for histidine analysis/measurement, all the other components may be provided in the form of being housed in the device. Alternatively, part of the components may be provided in the form of being housed in the device, whereas the rest may be provided in the form of not being housed in the device (e.g., the form of being housed in another container). In this case, the components not housed in the device may be used by being injected into the device when a target substance is measured.

Examples of the device include 1) a device including a first zone for mixing a sample and the component of (c) together to prepare a liquid mixture and a second zone for bringing the prepared liquid mixture into contact with the histidine decarboxylase and the 4-imidazolyl acetaldehyde generating enzyme to detect histidine (a device that performs mixing and detection processes in different zones); 2) a device including a zone for mixing a sample, the component of (c), and the histidine decarboxylase and the 4-imidazolyl acetaldehyde generating enzyme together and detecting histidine by the both enzymes (a device that performs mixing and detection processes in the same zone); and 3) a device including a channel that enables a sample, the component of (c) (and the both enzymes as needed) to be mixed together and a zone for detecting histidine by the both enzymes (a device that, when the sample is injected into an injection port of the device, sends the liquid via the channel, automatically mixes the sample and the like together, and automatically detects histamine in the obtained liquid mixture in the detection zone). In view of automatization, preferred is the device of 3), especially the device of 3) in the form of a microchannel device. In the device of 3), the histidine decarboxylase and the 4-imidazolyl acetaldehyde generating enzyme may be provided to the liquid flowing through the channel or provided in the form of being fixed to or placed at the detection zone and is provided in the form of being fixed to or placed at the detection zone.

The histidine decarboxylase may also be used, together with the 4-imidazolyl acetaldehyde generating enzyme, as the enzyme sensor for histidine analysis/measurement. The enzyme sensor for histidine analysis/measurement includes, for example, a detecting electrode, and the histidine decarboxylase and the 4-imidazolyl acetaldehyde generating enzyme that are immobilized to or disposed on the detecting electrode. Both enzymes are fixed to or placed at the electrode directly or indirectly.

Examples of the electrode for detection when the 4-imidazolyl acetaldehyde generating enzyme is a histamine dehydrogenase include an electrode for detecting hydrogen peroxide, and more specific examples include an oxidase type electrode for detecting hydrogen peroxide and a diaphragm type electrode for detecting hydrogen peroxide. With this electrode, hydrogen peroxide occurring when histamine is oxidized through the histamine dehydrogenase activity is detected, whereby measurement of histidine in the sample substance is enabled. For the other configuration, configurations employed for known sensors can be used as they are or in a modified manner as appropriate.

The present invention may be used for the prediction of suffering from or diagnosis of the diseases in the subject such as Crohn's disease, inflammatory bowel diseases such as ulcerative colitis, histidinemia, cardiac cachexia, and cancer. The histidine amount decreases in the patient of inflammatory bowel disease, cardiac cachexia, lifestyle disease, and cancer; on the other hand, the histidine amount increases in the patient having histidinemia. Accordingly, for example, upon comparing the histidine amount in the specimen measured by the above-mentioned measurement method with the standard amount of a healthy person, if the histidine amount in the specimen is less than the standard amount, it can be judged that the subject is suffered from inflammatory bowel disease or cardiac cachexia. Upon comparing the histidine amount in the specimen measured by the above-mentioned measurement method with the standard amount of a healthy person, if the histidine amount in the specimen is more than the standard amount, it can be judged that the subject is suffered from histidinemia.

If the subject is in a remission phase of ulcerative colitis, this can be used for evaluation of a recurrence risk of ulcerative colitis. For example, in the case where the subject is clearly in a remission phase of ulcerative colitis, the histidine amount in the specimen measured by the above-mentioned measurement method is compared with the standard amount of a healthy person. When the histidine amount in the specimen is less than the standard amount, the recurrence risk of ulcerative colitis can be judged high. By comparing with the standard that the risk is low when the amount is large, the recurrence risk of ulcerative colitis in the subject can be judged.

EXAMPLES

The present invention is further described in detail through the following examples; however, the present invention is not limited to the following examples.

Example 1: Expression and Purification of HisDC

A recombinant expression system of HisDC using *Escherichia coli* was constructed. First, a plasmid for recombinant expression was constructed. In order to acquire a gene encoding the amino acid sequence of HisDC (SEQ ID No: 3) derived from Photobacterium phosphoreurn (codon optimized HisDC: SEQ ID No: 2), a target gene was amplified in accordance with a standard PCR method using a DNA primer 1 (SEQ ID No: 4: 5' TATCGAAGGTCGT-CATATGACCACCC 3') and a DNA primer 2 (SEQ ID No: 5: 5' TTTGTTAGCAGCCGGATCCTTAGGC 3'). Next, restricted enzyme digestion of pET-16b (Merk & Co.) was performed by using NdeI (Takara Bio Inc.) and HindIII (Takara Bio Inc.), and deproteinization and removal of unnecessary DNA fragments were performed by using Wizard SV Gel and PCR Clean-up System (Promega Corp.). From the obtained product, in accordance with a standard method, a ligation product was obtained, and then a transformant of *Escherichia coli* XL-10 Gold was acquired. A plasmid was extracted from the transformant of *Escherichia coli* XL-10 Gold. Insertion of the target gene into the plasmid was confirmed in accordance with a standard DNA sequence analysis method using this plasmid as a template. By using the plasmid having the target gene inserted therein as a template of PCR, His-tag was added to the 3' terminal of the target gene in accordance with a standard PCR method using a DNA primer 3 (SEQ ID No: 6: 5' GCCGCACTCGAGCACCACCACCACCACCACTGAG-GATCCGGCTGCTAACAAAGCCC GAAAGGAAGC 3') and a DNA primer 4 (SEQ ID No: 7: 5' GGCTGCAATCAT-TTCACCG 3'). This plasmid was coupled by means of a DNA ligase to acquire a transformant of *Escherichia coli* XL-10 Gold, and the plasmid was extracted. In accordance with a standard DNA sequence analysis method using this plasmid as a template, insertion of the target gene into the plasmid was confirmed. A transformant of *Escherichia coli* BL21 (DE3) was acquired in accordance with a standard method. Hereinafter, the plasmid including HisDC sequence having His-tag added to the N and C terminals will be called pET-16b-HisDC, and the transformant of BL21 (DE3) with pET-16b-HisDC will be called pET-16b-HisDC-BL21 (DE3).

HisDC was prepared as follows. First, inoculation was performed from a glycerol stock of pET-16b-HisDC-BL21 (DE3) onto an LB plate including 100 μg/mL ampicillin, which was then followed by the static culturing thereof at 37° C. overnight. 6 mL of an LB liquid culture medium including 100 µg/mL ampicillin was put into a 50 mL tube, and a single colony on the LB plate was inoculated thereto, and then, this was cultured at 37° C. overnight. Into 25 mL of an LB liquid culture medium including 100 µg/mL ampicillin, 1 mL of the broth was added; and then, this was cultured at 37° C. by gyratory shaking until a value of OD600 reached about 0.6. After this was allowed to statically stand at 16° C. for 30 minutes, IPTG was added thereto so as to give a final concentration of 1.0 mM, and then the bacteria were collected after this had been cultured at 16° C. overnight by gyratory shaking.

The bacterial cells were suspended in a crushing buffer (50 mM Tris-HCl, 500 mM NaCl, 0.2 µM PLP, and pH 8.0) and were crushed using an ultrasonic crusher (BIORUPTOR, Cosmo Bio Co., Ltd.). This crushed liquid was subjected to centrifugation at 13,000×g for 15 minutes, and then, the supernatant was recovered and was purified by using His Spin Trap (GE Healthcare Japan Corp.). A washing buffer (50 mM Tris-HCl, 500 mM NaCl, 75 mM imidazole, and pH 8.0) and an elution buffer (50 mM Tris-HCl, 500 mM NaCl, 500 mM imidazole, and pH 8.0) were used. An eluted fraction was recovered and diluted with the elution buffer so as to give a concentration of 0.2 mg/mL.

Example 2: Mass Preparation of HisDC (Wild-Type and Mutant)

Mass preparation of HisDC (wild-type and mutant) was carried out as follows. First, inoculation was performed from a glycerol stock of pET-16b-HisDC-BL21 (DE3) onto an LB plate including 100 µg/mL ampicillin, which was then followed by the static culturing thereof at 37° C. overnight. 50 mL of an LB liquid culture medium including 100 µg/mL ampicillin was put into a 250 mL flask, and a single colony on the LB plate was inoculated thereto, and then, this was cultured at 37° C. overnight. Into 2 L of the LB liquid culture medium including 100 µg/mL ampicillin, 20 mL of the broth was added; and then, this was cultured at 37° C. by gyratory shaking until a value of OD600 reached about 0.6. After this was allowed to statically stand at 16° C. for 30 minutes, IPTG was added thereto so as to give a final concentration of 0.1 mM, and then, the bacteria were collected into a 50 mL tube after this was cultured at 16° C. overnight by gyratory shaking.

The bacterial cells were suspended in a crushing buffer (50 mM Tris-HCl, 500 mM NaCl, 0.2 µM PLP, and pH 8.0) and were crushed by using an ultrasonic crusher (INSONATOR, Kubota Corporation Co., Ltd.). This crushed liquid was subjected to centrifugation at 15,000×g for 30 minutes, and then, the supernatant was recovered and was purified by using Ni Sepharose 6 Fast Flow (GE Healthcare Japan Corp.). A washing buffer (50 mM Tris-HCl, 500 mM NaCl, 75 mM imidazole, 0.2 µM PLP, and pH 8.0) and an elution buffer (50 mM Tris-HCl, 500 mM NaCl, 500 mM imidazole, 0.2 µM PLP, and pH 8.0) were used. An eluted fraction was recovered and diluted with 50 mM Tris-HCl/pH 8.0 by a factor of 10 times. This was purified by means of an anion-exchange column using AKTA Explorer 10S and 6 mL of Resource Q at 4° C. Equilibration was performed by using 50 mM Tris-HCl/pH 8.0, and elution was performed by using 50 mM Tris-HCl/1 M NaCl/pH 8.0 with a NaCl concentration gradient method, and then, buffer replacement with 50 mM Tris-HCl/500 mM NaCl/20% glycerol/pH 8.0 was performed.

Example 3: Preparation of HisDC Mutant

The HisDC mutant was prepared as follows. Using the QuikChange Lightning site-Directed Mutagenesis Kits (Agilent Technologies), mutation introduction to a HisDC gene was performed in accordance with the protocol attached to the product by using pET-16b-HisDC as a template. When a plurality of mutations were introduced, a mutation was added using a plasmid, to which a mutation had been introduced, as a template. Using this mutation-introduced plasmid, recombinant expression and purification were performed in accordance with the method described in Example 1, whereby various HisDC mutants were acquired.

Example 4: Mutant Screening with Activity Measurement

Evaluations of the activities of HisDC (wild-type and mutant) prepared in Example 1 and Example 3 were performed in accordance with the following procedure. Each HisDC solution of 0.2 mg/mL was dispensed to a microtube, and then, this was incubated at a temperature of any one of 4° C., 30° C., 35° C., and 40° C. for 15 minutes. Next, to 5 µL of this HisDC was added a mixture of 25 µL of a 0.2 M sodium phosphate buffer with pH 6.5, 15 µL of ultrapure water, and 5 µL of a histidine solution, and then, the resulting mixed solution was incubated at 25° C. for 60 minutes. To 50 µL of this solution were added 50 µL of a histamine dehydrogenase (Check Color Histamine; Kikkoman Biochemifa Co.) and 50 µL of a test solution; and then, the temporal change of the absorbance at a wavelength of 470 nm of this resulting solution was measured for 30 minutes with a microplate reader (Varioskan LUX; ThermoFisher Scientific Co.). The results of the single, double and triple mutants are listed in Table, 7, Table 8, and Table 9, respectively. Relative activities compared with a control as well as the residual activities after heat treatment for 15 minutes at each temperature are also described in Tables. The controls used in these experiments were: the wild-type in Table 7, the C57S mutant in Table 8, and the C57S/C101V mutant in Table 9.

TABLE 7

Activities and residual activities after heat treatment of the wild-type and the single mutants of HisDC

|  | Relative activity compared with control | Residual activity after heat treatment at 30° C. for 15 minutes | Residual activity after heat treatment at 35° C. for 15 minutes |
| --- | --- | --- | --- |
| WT | 100% | 20% | 6% |
| W15F | 98% | 26% | 5% |
| N21H | 191% | 29% | 9% |
| Q22R | 129% | 16% | 5% |
| M43L | 658% | 20% | 3% |
| E55S | 199% | 21% | 2% |
| C57A | 427% | 16% | 3% |
| C57G | 694% | 43% | 8% |
| C57R | 80% | 24% | 9% |
| C57S | 1045% | 67% | 21% |
| C57T | 603% | 31% | 6% |
| S96G | 120% | 16% | 6% |
| M98V | 288% | 20% | 3% |
| C101A | 529% | 20% | 3% |
| C101S | 223% | 34% | 8% |
| C101V | 289% | 47% | 13% |
| Y102F | 148% | 53% | 14% |
| Y114F | 222% | 68% | 15% |
| L130I | 156% | 20% | 6% |
| I132L | 108% | 30% | 10% |
| I132M | 166% | 26% | 5% |
| Y147F | 128% | 39% | 7% |

TABLE 7-continued

Activities and residual activities after heat treatment
of the wild-type and the single mutants of HisDC

|  | Relative activity compared with control | Residual activity after heat treatment at 30° C. for 15 minutes | Residual activity after heat treatment at 35° C. for 15 minutes |
|---|---|---|---|
| M185T | 665% | 29% | 5% |
| M185L | 544% | 25% | 4% |
| M185I | 347% | 22% | 4% |
| M185S | 523% | 23% | 4% |
| M185A | 470% | 21% | 4% |
| Y196F | 129% | 21% | 4% |
| M234A | 137% | 16% | 6% |
| M279I | 426% | 9% | 3% |
| M280L | 328% | 12% | 3% |
| M280I | 727% | 14% | 1% |
| C282A | 447% | 19% | 3% |
| C282S | 208% | 29% | 19% |
| C282V | 776% | 35% | 10% |
| C319A | 929% | 32% | 9% |
| C319S | 654% | 34% | 12% |
| C319V | 312% | 22% | 4% |
| V327I | 132% | 29% | 7% |
| C330A | 577% | 29% | 11% |
| C330S | 398% | 24% | 4% |
| C330V | 622% | 27% | 4% |
| C340A | 155% | 19% | 5% |
| M377T | 308% | 19% | 4% |
| M377L | 150% | 20% | 6% |
| M377I | 498% | 19% | 3% |
| M377A | 112% | 32% | 10% |

TABLE 8

Activities and residual activities after heat treatment
of the C57S mutant and the double mutants of HisDC

|  | Relative activity compared with control | Residual activity after heat treatment at 35° C. for 15 minutes | Residual activity after heat treatment at 40° C. for 15 minutes |
|---|---|---|---|
| C57S | 100% | 21% | 2% |
| C57S/C101A | 117% | 25% | 2% |
| C57S/C101S | 121% | 60% | 8% |
| C57S/C101V | 118% | 98% | 71% |
| C57S/C282A | 121% | 31% | 2% |
| C57S/C282S | 113% | 9% | 1% |
| C57S/C282V | 120% | 52% | 5% |
| C57S/C319A | 120% | 65% | 6% |
| C57S/C319S | 121% | 59% | 5% |
| C57S/C319V | 122% | 51% | 4% |
| C57S/C330A | 115% | 74% | 17% |
| C57S/C330S | 114% | 96% | 36% |
| C57S/C330V | 116% | 100% | 55% |

TABLE 9

Activities and residual activities after heat treatment
of the C57S/C101V mutant and the triple mutants of HisDC

|  | Relative activity compared with control | Residual activity after heat treatment at 35° C. for 15 minutes | Residual activity after heat treatment at 40° C. for 15 minutes |
|---|---|---|---|
| C57S/C101V | 100% | 41% | 3% |
| C57S/C101V/C282A | 101% | 27% | 2% |
| C57S/C101V/C282V | 100% | 76% | 16% |
| C57S/C101V/C319A | 103% | 35% | 2% |
| C57S/C101V/C319S | 103% | 47% | 4% |
| C57S/C101V/C319V | 102% | 35% | 2% |
| C57S/C101V/C330A | 73% | 15% | 2% |
| C57S/C101V/C330S | 100% | 26% | 2% |

From the results in Table 7, it can be seen that the histidine decarboxylase activity and/or the stability of HisDC can be improved by the single mutations described in Table 7. From the results in Tables 8 and 9, it can be seen that the histidine decarboxylase activity and/or the stability of HisDC can be improved by the double mutations or the triple mutations described in Tables 8 and 9.

Example 5: Substrate Specificities

Substrate specificities of HisDC prepared in Example 2 (wild-type and mutants) were evaluated in accordance with the following procedure. HisDC of 0.6 mg/mL was prepared. 5 μL of HisDC, 25 μL of a 0.2 M sodium phosphate buffer with pH 6.5, 10 μL of ultrapure water, and 10 μL of each 100 μM amino acid solution were mixed. This solution was incubated at 25° C. for 60 minutes. To 50 μL of this solution were added 50 μL of a histamine dehydrogenase (Check Color Histamine; Kikkoman Biochemifa Co.) and 50 μL of a test solution; and then, the temporal change of the absorbance at a wavelength of 470 nm of this resulting solution was measured with a microplate reader (Varioskan LUX; ThermoFisher Scientific Co.). The relative activities of the wild-type and the C57S mutant relative to the absorbance value after 60 seconds of the measurement of the histidine solution as 100% are described in Table 10.

TABLE 10

Substrate specificities of the wild-type and the C57S mutant

|  | relative activity | |
|---|---|---|
|  | WT | C57S |
| His | 100% | 100% |
| Tyr | 0% | 0% |
| Asp | 0% | 0% |
| Asn | 0% | 0% |
| Glu | 0% | 0% |
| Pro | 0% | 0% |
| Ser | 0% | 0% |
| Gln | 0% | 0% |
| Arg | 0% | 0% |
| Thr | 0% | 0% |
| Met | 0% | 0% |
| Lys | 0% | 0% |
| Ala | 0% | 0% |
| Gly | 0% | 0% |
| Cys | 1% | 1% |
| Phe | 0% | 0% |
| Ile | 0% | 0% |
| Leu | 0% | 0% |
| Val | 0% | 0% |
| Trp | 0% | 0% |

From the results in Table 10, it can be seen that the mutant used in this Example retains the substrate specificity and that the substrate specificity of HisDC can be retained by introduction of the mutation included in this mutant.

Example 6: Thermal Stability

By using HisDC prepared in Example 2 (wild-type and mutants), the thermal stabilities were evaluated. HisDCs were prepared as 1 mg/mL solution; and these were incubated for 10 minutes at 4° C., 20° C., 25° C., 30° C., 35° C., 40° C., 45° C., 50° C., 55° C., 60° C., and 70° C., respectively. After HisDCs were diluted to 0.2 mg/mL, each activity was measured in accordance with the method described in Example 4 when 10 mM histidine solution was used as substrate. On the basis of the absorbance value of HisDC after 15 minutes of incubation at 4° C. as 100%, the relative activities of the wild-type and the C57S mutant to this at the respective temperatures were calculated. These results are indicated in FIG. 7. The Tm values (temperature that indicate 50% of the residual activity) of the wild-type and of the C57S mutant are listed in Table 11.

TABLE 11

Tm values of the wild-type and the C57S mutant

| | Tm(° C.) |
|---|---|
| WT | 40.7 |
| C57S | 52.9 |

Because the mutant used in this Example exhibits higher Tm value, it can be seen that the thermal stability of the mutants used in this Example is improved, and that introduction of the mutation included in this mutant can increase the thermal stability of HisDC.

Example 7: Long-Term Storage Stability

Figure 8:
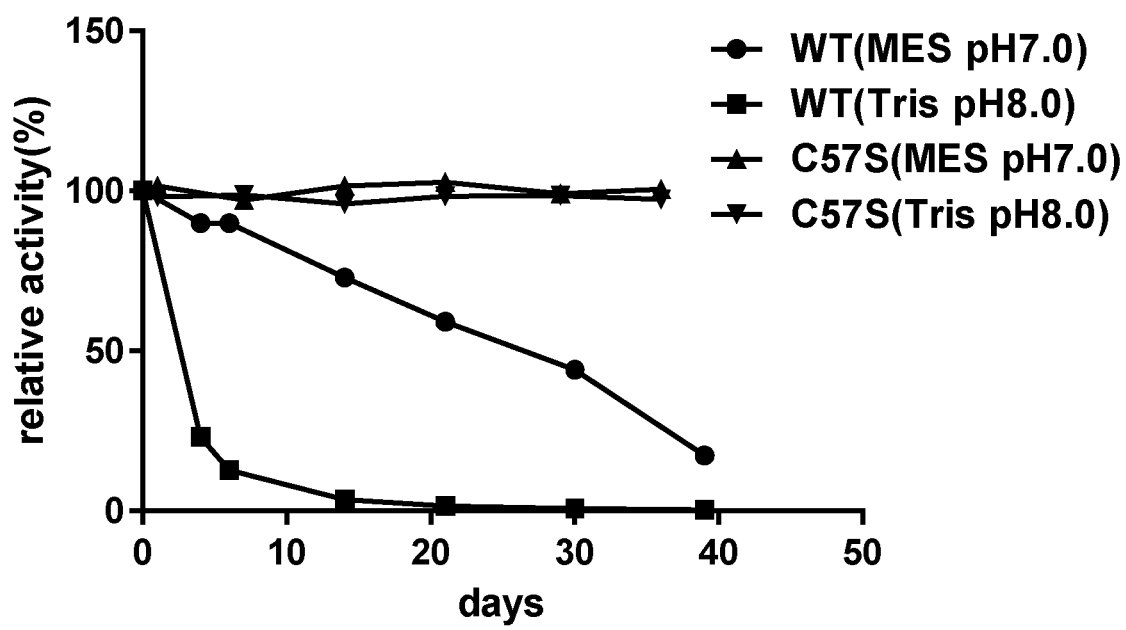
FIG. 8 shows the relative activities of the wild-type HisDC and the C57S mutant at each retention day in Example 7, indicating long-term storage stability.

The long-term storage stabilities of HisDC (wild-type and mutant) prepared in Example 2 were evaluated. HisDC was prepared as 0.2 mg/mL solution. Then, the buffer solutions of both the wild-type and the C57S mutant were exchanged with Tris-HCl/pH 8.0 and with MES/pH 7.0 by using a PD-10 column (GE Healthcare Japan Corp.). These HisDC enzyme solution was stored under a shading condition at 4° C.; and the activity was measured in accordance with the method of Example 4 at each day in which the starting date of the storage was regarded as the $0^{th}$ day. In FIG. 8, the changes of the activities of the wild-type HisDC and of the C57S mutant with the storage days in the respective buffer solutions are depicted in terms of the relative activities taken the activity of the 0th day as the control. From these results, it can be seen that the long-term storage stability of the mutant used in this Example is improved and that the long-term storage stability of HisDC can be improved by the mutation.

Example 8: Confirmation of Oxidation Resistance

Figure 9:
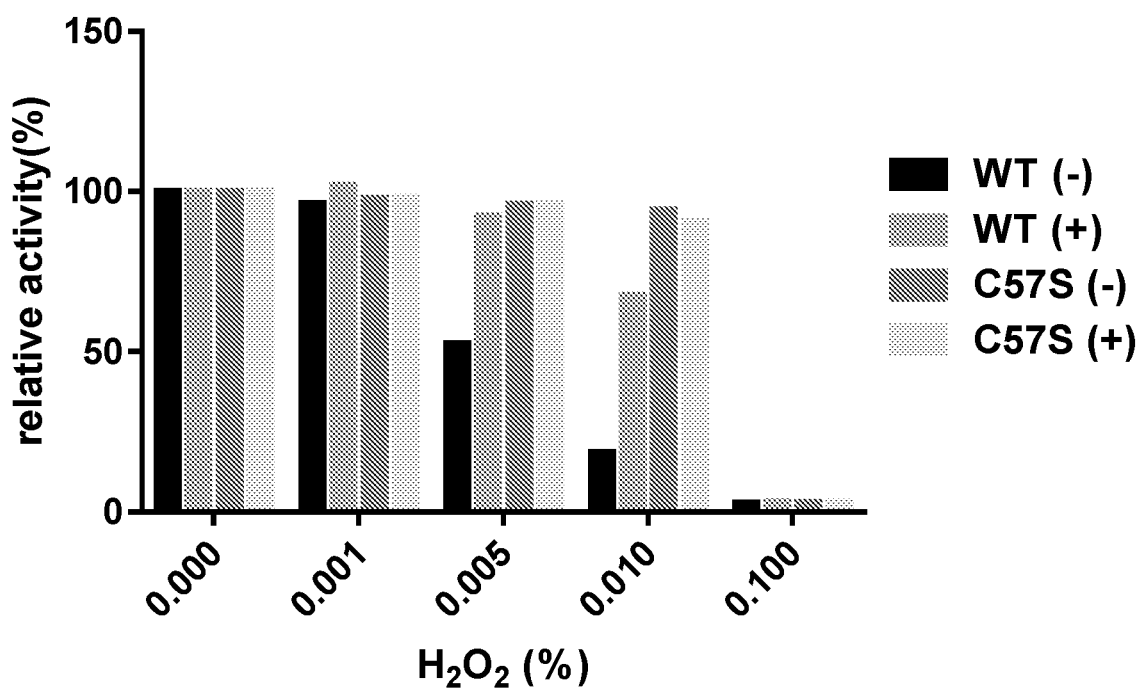
FIG. 9 shows the activities of the wild-type HisDC and the C57S mutant at each concentration of added hydrogen peroxide in Example 8, indicating oxidation resistance. In the diagram, (−) indicates the results without addition of ascorbic acid, and (+) indicates the results with addition of 1 mM ascorbic acid.

The oxidation resistances of HisDC (wild-type and mutant) prepared in Example 2 were evaluated. The buffer solutions of the wild-type HisDC and of the C57S mutant were displaced with 62.5 mM Tris-HCl/625 mM NaCl/pH 8.0 by using a PD-10 column (GE Healthcare Japan Corp.). The HisDC solution, a hydrogen peroxide solution, and an ascorbic acid solution were mixed with the ratio of 8:1:1; and then, this mixture was incubated at 35° C. for 15 minutes. The hydrogen peroxide solutions with the concentrations of 0%, 0.001%, 0.005%, 0.01%, or 0.1% as well as the ascorbic acid solution with the concentration of 1 mM were used. The activities of the HisDC solution treated with various conditions were measured basically in accordance with the method of Example 4. In FIG. 9, the activities of the wild-type HisDC and of the C57S mutant measured with these conditions are illustrated as the relative activities to the control experiment in which the concentration of the aqueous hydrogen peroxide solution was 0%. Here, (−) designates the results without addition of ascorbic acid, and (+) designates the results with addition of the 1 mM ascorbic acid. From these results, it can be seen that the oxidation resistance of the mutant used in this Example is improved and that the oxidation resistance of HisDC can be improved by introduction of the mutation included in this mutant.

From the results of Examples, it can be seen that the histidine enzyme activity of the mutated HisDC as described herein is improved from the wild-type so that this is useful for a quick and highly sensitive measurement of histidine and/or for production of histamine. In addition, the mutant has higher thermal stability and higher oxidation resistance than the wild-type, in particular, this can exhibit excellent thermal stability and oxidation resistance in a solution exhibiting excellent storage stability; and thus, this is useful as a histidine testing reagent, in particular, as a liquid histidine testing reagent.

Example 9: Confirmation of Oxidation Resistance

Figure 10:
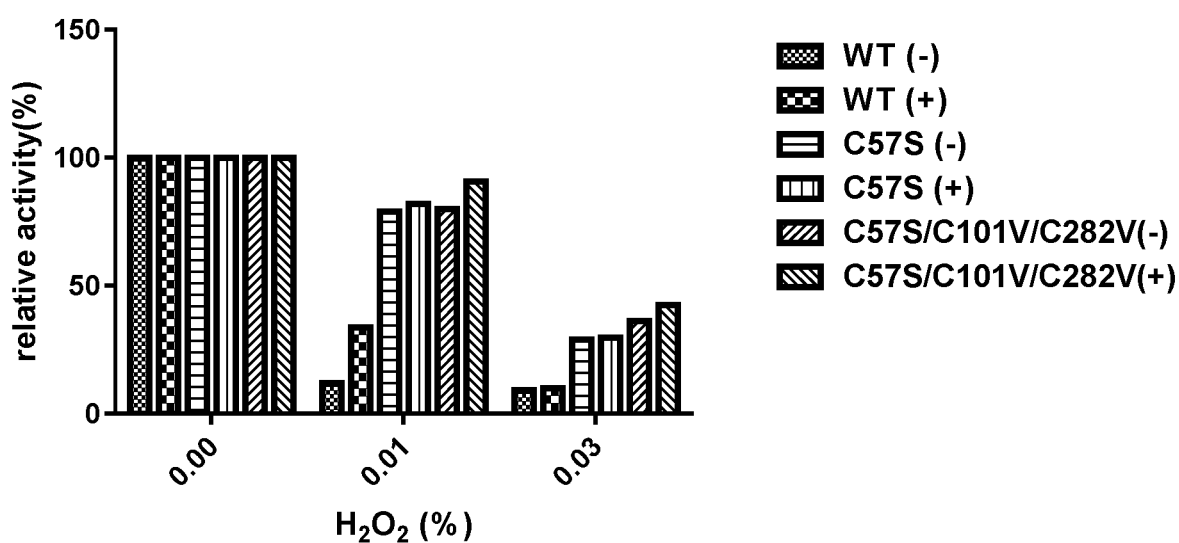
FIG. 10 shows the activities of the wild-type HisDC, the C57S mutant, and the C57S/C101V/C282V mutant at each concentration of added hydrogen peroxide in Example 9, indicating oxidation resistance. In the diagram, (−) indicates the results without addition of ascorbic acid, and (+) indicates the results with addition of 1 mM ascorbic acid.

The oxidation resistances of HisDC (wild-type and mutant) prepared in Example 2 were evaluated. The buffer solutions of the wild-type HisDC, of the C57S mutant, and of the C57S/C101V/C282V mutant were displaced with 62.5 mM Tris-HCl/625 mM NaCl/pH 8.0 by using a PD-10 column (GE Healthcare Japan Corp.). The HisDC solution, a hydrogen peroxide solution, and an ascorbic acid solution were mixed with the ratio of 8:1:1; and then, this mixture was incubated at 40° C. for 15 minutes. The hydrogen peroxide solutions with the concentrations of 0%, 0.01%, or 0.03% as well as the ascorbic acid solution with the concentration of 1 mM were used. The activities of the HisDC solution treated with various conditions were measured basically in accordance with the method of Example 4. In FIG. 10, the activities of the wild-type HisDC and of the C57S mutant measured with these conditions are illustrated as the relative activities to the control experiment in which the concentration of the hydrogen peroxide solution was 0%. Here, (−) designates the results without addition of ascorbic acid, and (+) designates the results with addition of the 1 mM ascorbic acid. From these results, it can be seen that the oxidation resistances of the mutants used in this Example are improved and that the oxidation resistances of HisDC can be improved by introduction of the mutations included in these mutants.

INDUSTRIAL APPLICABILITY

The present invention provides a mutated HisDC, which is useful for quick, highly sensitive, and specific measurement of histidine or production of histamine and use thereof. Consequently, the present invention is useful in wide fields such as biological research, health and nutrition, medical treatment, and food manufacturing.

The invention claimed is:

1. A polynucleotide encoding a mutated histidine decarboxylase wherein said mutated histidine decarboxylase comprises a motif selected from the group consisting of:
   A) Motif (1): $GDWX_1X_2X_3CNYX_4$ motif (SEQ ID No: 8), where $X_1$ is A, S, or G; $X_2$ is E, A, or D; $X_3$ is Y or E, and $X_4$ is L or R,
   B) Motif (2): $EX_5NX_6X_7X_8CYLX_9$ motif (SEQ ID No: 9), where $X_5$ is S or G, $X_6$ is M or L, $X_7$ is F or Y, $X_8$ is G or S, and $X_9$ is G, S, or A,
   C) Motif (3): $GSRNGX_{10}TPX_{11}X_{12}MWX_{13}AX_{14}X_{15}S$ motif (SEQ ID No: 10), where $X_{10}$ is H or Q, $X_{11}$ is L or M, $X_{12}$ is M or I, $X_{13}$ is C, E or A, $X_{14}$ is V or I, and $X_{15}$ is K or R,
   D) Motif (4): $GX_{16}X_{17}AWX_{18}X_{19}$ motif (SEQ ID No: 11), where $X_{16}$ is I or V, $X_{17}$ is N, D, Q, H, or P, $X_{18}$ is C, R, or L, and $X_{19}$ is N, H, or C,
   E) Motif (5): $TVX_{20}FPCPSX_{21}X_{22}$ motif (SEQ ID No: 12), where $X_{20}$ is V or I, $X_{21}$ is E, V, or A, and $X_{22}$ is A, D, S, or N,
   F) Motif (6): $VWKX_{23}X_{24}CLAX_{25}S$ motif (SEQ ID No: 13), where $X_{23}$ is K or R, $X_{24}$ is H or Y, and $X_{25}$ is T or I, and
   G) combinations thereof;
   wherein at least one amino acid residue in the selected motif is mutated as compared to a wild-type histidine decarboxylase;
   wherein said mutated histidine decarboxylase has higher histidine decarboxylase activity and/or stability than a wild-type histidine decarboxylase;
   wherein the wild-type histidine decarboxylase comprises SEQ ID No: 3; and
   wherein said mutated histidine decarboxylase comprises an amino acid sequence having at least 90% or more amino acid sequence identity to the amino acid sequence of the wild-type histidine decarboxylase.

2. The polynucleotide according to claim 1, wherein the at least one amino acid residue in the Motifs (1) to (6) is selected from the group consisting of a sulfur-containing amino acid residue, an aromatic amino acid residue, an acidic amino acid residue, a hydroxy group-containing amino acid residue, an amide group-containing amino acid residue, a branched chain amino acid residue, and combinations thereof; and
   wherein the at least one amino acid in the Motifs (1) to (6) is mutated as compared to the wild-type histidine carboxylase.

3. The polynucleotide according to claim 2, wherein
   the sulfur-containing amino acid residue is selected from the group consisting of cysteine, methionine, and combinations thereof;
   the aromatic amino acid residue is selected from the group consisting of tryptophan, phenylalanine, histidine, tyrosine, and combinations thereof;

the acidic amino acid residue is selected from the group consisting of glutamic acid, aspartic acid, and combinations thereof;

the hydroxy group-containing amino residue acid is selected from the group consisting of serine, threonine, and combinations thereof;

the amide group-containing amino acid residue is selected from the group consisting of asparagine, glutamine, and combinations thereof; and the branched chain amino acid residue is selected from the group consisting of valine, leucine, isoleucine, and combinations thereof.

4. The polynucleotide according to claim 2, wherein the sulfur-containing amino acid residue is substituted with an amino acid residue selected from the group consisting of alanine, glycine, serine, threonine, arginine, lysine, histidine, isoleucine, leucine, and valine;

the aromatic amino acid residue is substituted with an amino acid residue selected from the group consisting of phenylalanine, tyrosine, tryptophan, histidine, asparagine, glutamine, lysine, and arginine;

the acidic amino acid residue is substituted with a serine or threonine;

the hydroxy group-containing amino acid residue is substituted with a glycine or alanine;

the amide group-containing amino acid residue is substituted with an amino acid residue selected from the group consisting of phenylalanine, tyrosine, tryptophan, histidine, arginine, lysine, serine, and threonine; and the branched chain amino acid residue is substituted with an amino acid residue selected from the group consisting of isoleucine, leucine, and methionine.

5. An expression vector comprising the polynucleotide according to claim 1.

6. A transformant comprising the expression vector according to claim 5.

7. A method for producing a mutated histidine decarboxylase, the method comprising:

producing a modified histidine decarboxylase encoding a mutated histidine decarboxylase using the transformant according to claim 6, wherein said mutated histidine decarboxylase comprises a motif selected from the group consisting of:

A) Motif (1): $GDWX_1X_2X_3CNYX_4$ motif (SEQ ID No: 8), where $X_1$ is A, S, or G; $X_2$ is E, A, or D; $X_3$ is Y or E, and $X_4$ is L or R, B) Motif (2): $EX_5NX_6X_7X_8CYLX_9$ motif (SEQ ID No: 9), where $X_5$ is S or G, $X_6$ is M or L, $X_7$ is F or Y, $X_8$ is G or S, and $X_9$ is G, S, or A, C) Motif (3): $GSRNGX_{10}TPX_{11}X_{12}MWX_{13}AX_{14}X_{15}S$ motif (SEQ ID No: 10), where $X_{10}$ is H or Q, $X_{11}$ is L or M, $X_{12}$ is M or I, $X_{13}$ is C, E or A, $X_{14}$ is V or I, and $X_{15}$ is K or R, D) Motif (4): $GX_{16}X_{17}AWX_{18}X_{19}$ motif (SEQ ID No: 11), where $X_{16}$ is I or V, $X_{17}$ is N, D, Q, H, or P, $X_{18}$ is C, R, or L, and $X_{19}$ is N, H, or C, E) Motif (5): $TVX_{20}FPCPSX_{21}X_{22}$ motif (SEQ ID No: 12), where $X_{20}$ is V or I, $X_{21}$ is E, V, or A, and $X_{22}$ is A, D, S, or N, F) Motif (6): $VWKX_{23}X_{24}CLAX_{25}S$ motif (SEQ ID No: 13), where $X_{23}$ is K or R, $X_{24}$ is H or Y, and $X_{25}$ is T or I, and G) combinations thereof;

wherein at least one amino acid residue in the selected motif is mutated as compared to a wild-type histidine decarboxylase;

wherein said mutated histidine decarboxylase has higher histidine decarboxylase activity and/or stability than a wild-type histidine decarboxylase;

wherein the wild-type histidine decarboxylase comprises SEQ ID No: 3;

wherein said mutated histidine decarboxylase comprises an amino acid sequence having at least 90% or more amino acid sequence identity to the amino acid sequence of the wild-type histidine decarboxylase.

* * * * *